United States Patent [19]

Diamond et al.

[11] Patent Number: 5,692,220
[45] Date of Patent: Nov. 25, 1997

[54] DECISION SUPPORT SYSTEM AND METHOD FOR DIAGNOSIS CONSULTATION IN LABORATORY HEMATOPATHOLOGY

[75] Inventors: Lawrence W. Diamond; Doyen T. Nguyen, both of Cologne, Germany

[73] Assignee: Coulter Corporation, Miami, Fla.

[21] Appl. No.: 116,131

[22] Filed: Sep. 2, 1993

[51] Int. Cl.$^6$ ........................................... A61B 5/00
[52] U.S. Cl. ............................. 395/924; 128/630
[58] Field of Search .................. 364/413.07, 413.08, 364/413.02; 128/630, 920, 921, 924; 436/63, 17, 172; 382/6; 395/54, 60, 64, 924

[56] References Cited

U.S. PATENT DOCUMENTS

| | | | |
|---|---|---|---|
| 4,404,683 | 9/1983 | Kobayashi et al. | 364/413.08 |
| 4,702,595 | 10/1987 | Mutschler et al. | 364/413.08 |
| 4,706,207 | 11/1987 | Hennessy et al. | 364/413.08 |
| 4,850,024 | 7/1989 | Motoike et al. | 364/413.08 |
| 5,023,785 | 6/1991 | Adrion et al. | 364/413.08 |
| 5,031,099 | 7/1991 | Marshall et al. | 364/413.08 |
| 5,040,112 | 8/1991 | Kettler | 364/413.08 |
| 5,137,809 | 8/1992 | Loken et al. | 435/7.21 |
| 5,234,816 | 8/1993 | Terstappen | 435/7.24 |

OTHER PUBLICATIONS

"Computer-Assisted Bone Marrow Interpretation: A Pattern Approach," Proceedings of MIE 93, Apr., 1993, D.T. Nguyen et al., pp. 119–123.

"Evaluation of a Knowledge-Based System for Interpreting Flow Cytometric Immunophenotyping Data," proceedings of MIE 93, Apr., 1993, L.W. Diamond et al., pp. 124–128.

"Today's Life Science" Methods, entitled Computer-Assisted Interpretive Reporting in Haematology by Lawrence W. Diamond and Doyen T. Nguyen, Mar., 1993, pp. 52–58.

"The British Journal of Healthcare Computing" Conference Proceedings for Current Perspectives in Healthcare Computing 1993, Harrogate 15–17 Mar., for The British Computer Society Health Informatics Specialist Groups entitled Communication between Expert Systems in Haematology by L.W. Diamond and D.T. Nguyen (Laboratoire d'Hematologie, Hopital Henri Mondor, 94010, Creteil, France), cover page with article pp. of 111–119.

"Methods of Information in Medicine," vol. 31, No.2, 1992, entitled Expert System Design in Hematology Diagnosis by D.T. Nguyen, L.W. Diamond, G. Priolet and C. Sultan (Laboratoire d'Hematologie, Hopital Henri Mondor, 94010, Creteil, France), pp. 82–89, Jul., 1992.

"MEDINFO 92" Elsevier Science Publishers B.V. (North-Holland), entitled A Decision Support System for Diagnostic Consultation In Laboratory Hematology by Nguyen D.T., Diamond L.W., Priolet G. and Sultan C. (Laboratoire d'Hematologie, Hopital Henri Mondor, 51 Avenue du Mal de Lattre de Tassigny, 94010, Creteil, France), pp. 591–595, Sep. 5, 1992.

(List continued on next page.)

Primary Examiner—Jack B. Harvey
Assistant Examiner—David A. Wiley
Attorney, Agent, or Firm—A. Jose Cortina; Warren W. Kurz

[57] ABSTRACT

A system and method of diagnosis provides that data from a hematopathology analyzer, e.g., hematology analyzer and/or other blood testing instrument or test, is input and compared with patterns corresponding to specific patient conditions. The matched patterns are arranged in a hierarchy in accordance with predetermined rules. Initially the patterns matched are displayed, optionally with recommendations for additional testing. If additional testing is done, a comparison of the original test data and new data is done, the patterns matched and at least one highest ranked pattern is identified, optionally with a differential diagnosis.

18 Claims, 14 Drawing Sheets

OTHER PUBLICATIONS

Proceedings of "*MIE 93*" Eleventh International Congress of the European Federation for Medical Informatics (Jerusalem,Isreal—Apr. 18–22, 1993) entitled Computer–Assisted Bone Marrow Interpretation: A Pattern Approach by D.T. Nguyen, P. Cherubino, PB. Tamino and L.W. Diamond (Institute for Pathology, University of Cologne, Cologne, Germany), pp. 119–123.

Article entitled "Evaluation of a Knowledge–Based System for Interpreting Flow Cytometric Immunophenotyping Data" by L.W. Diamond, D.T. Nguyen, H. Jouault and M. Imbert (Laboratoire d'Hematologie, Hopital Henri Mondor, 94010, Creteil, France), 1993, pp. 124–128.

| | | | | | |
|---|---|---|---|---|---|
| NAME: | C.M. | ID NUMBER: | 09990007 | AGE: | 87 |
| DATE/TIME: | 3/26/1992 12:12:12 | SEQUENCE #: | 0999 | SEX: | F |
| CASS/POS: | 000003 | DATE OF BIRTH: | 3/3/1905 | | |
| USER FIELD 1: | | LOCATION: | HHM 752 | | |
| USER FIELD 2: | | PHYSICIAN | Dr. F.C. | | |
| USER FIELD 3: | | COMMENTS: | | | |

| | | |
|---|---|---|
| RBC: | 2.55 | Suspect Flags |
| Hgb: | 8.4 | ☐ BLASTS |
| Hct: | 26.7 | |
| MCV: | 104.6 | ☐ IMMATURE GRANULOCYTES/BANDS |
| MCH: | 32.8 | |
| MCHC: | 31.4 | ☐ VARIANT LYMPHS |
| RDW: | 38.2 | ☒ NRBCs |
| PLT: | 668 | |
| WBC: | 7.4 | ☒ DIMORPHIC RBC |
| Neut: | 5.2 | |
| Lymph: | 1.4 | ☒ MICRO RBCs/RBC FRAGMENTS |
| Mono: | 0.7 | |
| Eos: | 0.1 | ☐ RBC AGGLUTINATION |
| Baso: | 0.0 | ☐ PLATELET CLUMPS |
| WBC POPULATION: | NORMAL | |
| RBC POPULATION: | ABNORMAL | |
| PLT POPULATION: | ABNORMAL | |

[ ENTER MANUAL COUNTS ]

[ CHOOSE NEW CASE ]   [ PROCEED ]

FIG. 5

Professor Petrushka's Preliminary Comments

```
Case identification... 09990007 C.M.

In this 87 year old female the preliminary hemogram findings are consistent with
a MACROCYTIC PATTERN with
Moderate Normochromic Macrocytic Anemia
Marked Anisocytosis
Mild Thrombocytosis Scan the peripheral blood smear (20X objective).
Pay attention to RBC and WBC morphology (50X objective).
If abnormal cells are seen on scan, a manual WBC differential is recommended.
```

RBC    ☐ Agglutination    ☐ Rouleaux    ☒ NRBCs

WBC    ┌─Accept automated differential?─┐
       │  ◯ Yes        ⦿ No             │
       └────────────────────────────────┘

PLT    ☐ Platelet Clumping

Morphologic review necessary?    ☒ RBC    ☒ WBC    ☐ PLT

[ A manual differential is recommended when many NRBCs are present ]    [ Proceed ]

FIG. 6

Professor Petrushka's Preliminary Comments

Case identification... 09990007 C.M.

In this 87 year old female the preliminary hemogram findings are consistent with
a MACROCYTIC PATTERN with
Moderate Normochromic Macrocytic Anemia
Marked Anisocytosis
Mild Thrombocytosis Scan the peripheral blood smear (20X objective).
Pay attention to RBC and WBC morphology (50X objective).
If abnormal cells are seen on scan, a manual WBC differential is recommended.

RBC ☐ Agglutination ☐ Rouleaux ☐ NRBCs

WBC — Accept automated differential? —
    ● Yes    ○ No

PLT ☐ Platelet Clumping

Morphologic review necessary?  ☒ RBC  ☐ WBC  ☐ PLT

[ Proceed ]

FIG. 7

| | | | |
|---|---|---|---|
| NAME: | D.H. | ID NUMBER: 07603942 | AGE: 73 |
| DATE/TIME: | 4/22/1990 09:41:08 | SEQUENCE #: 0417 | SEX: F |
| CASS/POS: | 001108 | DATE OF BIRTH: 3/12/1917 | |
| USER FIELD 1: | | LOCATION: HHM 223 | |
| USER FIELD 2: | | PHYSICIAN: Dr. R.C. | |
| USER FIELD 3: | | COMMENTS: | |

| | |
|---|---|
| RBC: | 2.74 |
| Hgb: | 9.0 |
| Hct: | 26.9 |
| MCV: | 98.1 |
| MCH: | 32.7 |
| MCHC: | 33.4 |
| RDW: | 14.0 |
| PLT: | 262 |
| WBC: | 25.5 |
| Neut: | 0.7 |
| Lymph: | 23.5 |
| Mono: | 1.1 |
| Eos: | 0.1 |
| Baso: | 0.1 |
| WBC POPULATION: | ABNORMAL |
| RBC POPULATION: | ABNORMAL |
| PLT POPULATION: | NORMAL |

Suspect Flags

☒ BLASTS

☒ IMMATURE GRANULOCYTES/BANDS 1

☒ VARIANT LYMPHS

☐ NRBCs

☐ DIMORPHIC RBC

☐ MICRO RBCs/RBC FRAGMENTS

☐ RBC AGGLUTINATION

☐ PLATELET CLUMPS

[ ENTER MANUAL COUNTS ]

[ CHOOSE NEW CASE ]     [ PROCEED ]

FIG. 8

Professor Petrushka's Preliminary Comments

Case identification... 07603942 D.H.
In this 73 year old female the preliminary hemogram findings are consistent with
an ABNORMAL MONONUCLEAR CELL PATTERN with
Moderate Normochromic Normocytic Anemia
Mild Leukocytosis
Neutropenia (without Leukopenia)
Severe Lymphocytosis
Monocytosis Scan the peripheral blood smear (20X objective).
Pay attention to RBC and WBC morphology (50X objective).
A manual WBC differential is recommended.
If no blasts or variant lymphs are seen on scan, the manual differential may not be
necessary.

RBC  ☐ Agglutination  ☐ Rouleaux  ☐ NRBCs

WBC  Accept automated differential?
      ○ Yes    ⦿ No

PLT  ☐ Platelet Clumping

Morphologic review necessary?  ☒ RBC  ☒ WBC  ☐ PLT

[Proceed]

FIG. 9

| Spherocytes | ⦿ 0 ○ 1+ ○ 2+ ○ 3+ |
| Target Cells | ⦿ 0 ○ 1+ ○ 2+ ○ 3+ |
| Teardrop Cells | ⦿ 0 ○ 1+ ○ 2+ ○ 3+ |
| Sickle Cells | ⦿ 0 ○ 1+ ○ 2+ ○ 3+ |
| Schistocytes | ⦿ 0 ○ 1+ ○ 2+ ○ 3+ |
| Ellip/Ovalocytes | ⦿ 0 ○ 1+ ○ 2+ ○ 3+ |
| Stomatocytes | ⦿ 0 ○ 1+ ○ 2+ ○ 3+ |
| Acanthocytes | ⦿ 0 ○ 1+ ○ 2+ ○ 3+ |
| Echinocytes | ⦿ 0 ○ 1+ ○ 2+ ○ 3+ |
| Bite Cells | ⦿ 0 ○ 1+ ○ 2+ ○ 3+ |

| Polychromasia | ○ 0 ⦿ 1+ ○ 2+ ○ 3+ |
| Hypochromia | ⦿ 0 ○ 1+ ○ 2+ ○ 3+ |
| Microcytes | ⦿ 0 ○ 1+ ○ 2+ ○ 3+ |
| Macrocytes | ○ 0 ⦿ 1+ ○ 2+ ○ 3+ |
| Basophilic Stippling | ⦿ 0 ○ 1+ ○ 2+ ○ 3+ |
| Howell Jolly | ⦿ 0 ○ 1+ ○ 2+ ○ 3+ |

Dimorphism            ☐ Present
Double population     ☐ Present
Intracellular organisms  ☐ Present
Extracellular organisms  ☐ Present WBC or PLT Morphology/Differential Required?
⦿ Yes    ○ No

[Proceed]

FIG. 10

| | | | |
|---|---|---|---|
| Neutrophils | 3 | Hyposegmentation | ☐ Present |
| Bands | | Hypersegmentation | ☐ Present |
| Lymphocytes | 11 | Hypogranulation | ☐ Present |
| Monocytes | | Toxic Granulation | ☐ Present |
| Eosinophils | | Auer Rods | Present ⇩ |
| Basophils | | WBC inclusions | ☐ Present |
| NRBCs | | | |
| | | Giant Platelets | ☐ Present |
| Blasts | 86 | Micromegakaryocytes | ☐ Present |
| Promyelocytes | | | |
| Myelocytes | | | |
| Metamyelocytes | | | |
| Other MNCs | | Manual Platelet | |

☐ Variant lymphs   ☐ Plasmacytoid lymphs   ☐ Large granular lymphs   ☐ Smudge Cells Review Morphology   ☒ WBC   ☐ PLT
Manual Diff/Count   ☒ WBC   ☐ PLT

[ Proceed ]

FIG. 11

Professor Petrushka's Interpretation and Recommendations

Case identification... 07603942 D.H.

In this 73 year old female the hemogram findings are characteristic of
an ABNORMAL MONONUCLEAR CELL PATTERN with
Moderate Normochromic Normocytic Anemia
Mild Leukocytosis
Neutropenia (without Leukopenia)

The differential diagnosis includes: ACUTE LEUKEMIA.

The presence of blasts with Auer rods is highly suggestive of an ACUTE MYELOID LEUKEMIA.

The following tests may be helpful: BONE MARROW ASPIRATE/BIOPSY with CYTOGENETIC analysis. CYTOCHEMICAL STAINS (Myeloperoxidase, NSE) on blood or bone marrow smears.
IMMUNOPHENOTYPING (by FLOW CYTOMETRY) on blood or bone marrow.

FIG. 12   [ Choose New Case ]   [ Next Case ]

| Flow Cytometry Data Entry | | | |
|---|---|---|---|

Case # [ ]  Date (mm/dd/yy) [ ]  Patient ID# [ ]

Name [ ]  Sex [ ]  DOB (mm/dd/yy) [ ]

Specimen ○ PB  ○ BM  ○ LN  ○ FL  ○ SP  ○ EN

| | | | | | | |
|---|---|---|---|---|---|---|
| CD1a | [ ] | CD19 | [ ] | Gly A | [ ] | % Blasts [ ] |
| CD2 | [ ] | CD20 | [ ] | cKappa | [ ] | |
| CD3 | [ ] | CD22 | [ ] | cLambda | [ ] | Abn Mononuclear Cells |
| CD4 | [ ] | CD25 | [ ] | Tdt | [ ] | Burkitt's Cells |
| CD5 | [ ] | CD33 | [ ] | MPO Ab | [ ] | Cerebriform Cells |
| CD7 | [ ] | CD34 | [ ] | cCD3 | [ ] | Flower Cells |
| CD8 | [ ] | CD41 | [ ] | cCD22 | [ ] | Hairy Cells |
| CD10 | [ ] | CD56 | [ ] | c mu | [ ] | Lymphoma Cells |
| CD11c | [ ] | CD57 | [ ] | MPO Cyto | [ ] | None |
| CD13 | [ ] | CD61 | [ ] | CD45 | [ ] | Plasma Cells |
| MY4 | [ ] | Kappa | [ ] | CD71 | [ ] | Plasmablasts |
| Mo2 | [ ] | Lambda | [ ] | | | Prolymphocytes |
| CD16 | [ ] | Ia | [ ] | | | |

% Abn Cells [ ]  Cell Size [ ]

DNA Index [ ]  Total S% [ ]

Tumor S% [ ]  [ OK ]  [ Cancel ]

FIG. 13

| | | | | |
|---|---|---|---|---|
| Name: | F.B. | ID Number: | SM027236l | Additional Information |
| Sex: | M | Date of Birth: | 1/1/1924 | |
| Specimen: | LN | Specimen Date: | 2/27/1992 | |
| Specimen Number: | RB11250 | | | |

| | | | | |
|---|---|---|---|---|
| CD1a: | | CD61: | | Professor Fidelio's Interpretation: |
| CD2: | − | Kappa: | − | |
| CD3: | − | Lambda: | + | The immunophenotype is characteristic of a MATURE B-CELL PATTERN MONOCLONAL for LAMBDA. |
| CD4: | − | Ia(HLA-DR): | + + | |
| CD5: | + | Glycophorin A: | | |
| CD7: | − | cKappa: | | |
| CD8: | − | cLambda: | | In a lymph node, the differential diagnosis for this pattern includes: B-cell non-Hodgkin's Lymphomas. |
| CD10: | − | Tdt: | | |
| CD11c: | − | MPO Ab: | | |
| CD13: | − | cCD3: | | |
| MY4: | | cCD22: | | CD5 positivity and weak surface immunoglobulin staining are highly suggestive of small lymphocytic lymphoma/CLL. |
| Mo2: | − | c mu: | | |
| CD16: | | MPO cyto: | | |
| CD19: | + + | CD45: | + + + | |
| CD20: | + + | CD71: | + | |
| CD22: | | Size Abn Cells: | Small | The small cell size and low S-phase are consistent with the above diagnosis. |
| CD25: | + | %Abn Cells: | 61 | |
| CD33: | − | DNA Index: | 1.0 | |
| CD34: | − | Total S%: | 1.0 | |
| CD41: | | Tumor S%: | | The results should be correlated with the lymph node biopsy, clinical features, and appropriate laboratory studies. |
| CD56: | − | | | |
| CD57: | | | | |
| | | Next Case | | |

FIG. 14

| | | | | | |
|---|---|---|---|---|---|
| Name: | N.B. | | ID Number: | HHM097 | Additional Information |
| Sex: | M | | Date of Birth: | 4/10/1976 | |
| Specimen: | PB | | Specimen Date: | 3/15/1990 | L3 |
| Specimen Number: | EX004 | | | | |

| | | | | |
|---|---|---|---|---|
| CD1a: | 1 | CD61: | | |
| CD2: | 7 | Kappa: | 83 | |
| CD3: | 8 | Lambda: | 3 | |
| CD4: | 4 | Ia(HLA-DR): | 83 | |
| CD5: | 5 | Glycophorin A: | | |
| CD7: | 3 | cKappa: | | |
| CD8: | 4 | cLambda: | | |
| CD10: | | Tdt: | | |
| CD11c: | | MPO Ab: | | |
| CD13: | 2 | cCD3: | | |
| MY4: | 4 | cCD22: | | |
| Mo2: | | c mu: | | |
| CD16: | | MPO cyto: | | |
| CD19: | 70 | CD45: | | |
| CD20: | 68 | CD71: | | |
| CD22: | | Size Abn Cells: | | |
| CD25: | | %Abn Cells: | | |
| CD33: | 1 | DNA Index: | | |
| CD34: | 1 | Total S%: | | |
| CD41: | 1 | Tumor S%: | | |
| CD56: | | | | |
| CD57: | | | | |

Next Case

Professor Fidelio's Interpretation:

The immunophenotype is characteristic of a MATURE B-CELL PATTERN MONOCLONAL for KAPPA.

In the peripheral blood, the differential diagnosis for this pattern includes: B-ALL(L3) and B-CELL lymphoproliferative disorders.

The combination of a mature B-cell phenotype and blasts with Burkitt's cell morphology is consistent with a diagnosis of B-ALL(L3)

The results should be confirmed with a bone marrow aspirate/biopsy and correlated with the clinical features and appropriate laboratory studies.

FIG. 15

| | | | | | | |
|---|---|---|---|---|---|---|
| Name: | B.D. | ID Number: | HHM162 | | Date: | 3/9/93 |
| Sex: | F | Case #: | B001 | | Age: | 83 |
| Physician: | | History: | | | | |

Specimen    ☒ Aspirate        ☐ Biopsy        ☐ Touch Prep

Peripheral Blood Findings

| | | | | | |
|---|---|---|---|---|---|
| Hgb: | 10.0 | Neut: | 13% | Blasts: | 70% |
| MCV: | 95.0 | Bands: | | Pro: | |
| MCH: | 33.0 | Lymph: | 15% | Myel: | 1% |
| RDW: | 19.6 | Mono: | | Meta: | 1% |
| PLT: | 61 | Eos: | | MNCs: | |
| WBC: | 159.0 | Baso: | | Morph: | |

Recommendations

> Peripheral Blood(12/13/1988):ABNORMAL MONONUCLEAR CELL PATTERN.
> In the presence of circulating blasts, an ACUTE LEUKEMIA must be excluded.
> If the bone marrow demonstrates an ACUTE LEUKEMIA, the following studies are
> recommended: CYTOCHEMISTRIES, IMMUNOPHENOTYPING, CYTOGENETICS. If
> the diagnosis is ALL, DNA ANALYSIS may be helpful.

Approve CBC Results?
◉ Yes    ○ No        [Choose New Case]    [Proceed]

FIG. 16

Low Power Evaluation

Spicules: ◉ Present  ○ Absent        Megakaryocytes: ○ Normal  ◉ Decreased  ○ Increased Cellularity(%)  [⇦       ⇨]  100%

Foreign Cells  [         ⇩]

(50X Oil Objective)   [Differential]

| | | | | | |
|---|---|---|---|---|---|
| Blasts: | 65 | Monocytes: | | Early erythroid: | |
| Promyelocytes: | | Eosinophils: | | Late erythroid: | 16 |
| Myelocytes: | | Basophils: | | MNC (%): | |
| Metamyelocytes: | | Lymphocytes: | 18 | MNC Type: | |
| Neutrophils/Bands: | 1 | Plasma Cells: | | ☐ Organisms | |

Qualitative Abnormalities        Monocyte-like morphology

☐ Erythroid Karryorhexis   ☐ Hypogranulation   ☐ Abnormal Eosinophils

N/C Asynchrony  [         ⇩]    Giant Precursors  [         ⇩]

Cytoplasmic Vacuoles  [         ⇩]    [Special Stains]   [Proceed]

FIG. 17

Aspirate

Iron Storage
○ Normal   ○ Decreased   ○ Increased

Iron Incorporation
○ Normal   ○ Decreased   ○ Increased

Ring Sideroblasts (%)   [⇦      ⇨]   Not Done

Stains for Blasts and Abnormal Mononuclear Cells

Peroxidase
○ Negative   ● Positive     NSE [⇦      ⇨] 90%

☐ PAS Positive     ☐ TRAP Positive

Biopsy

Reticulin
○ 0   ○ 1+   ○ 2+   ○ 3+

Positive for Organisms  [        ⇩]          [Proceed]

FIG. 18

Professor Belmonte's Interpretation and Recommendations

Peripheral Blood: Hgb 10.0, MCV 95.0, MCH 33.0, PLT 61, WBC 159.0
Manual Differential: 13% Neutrophils, 15% Lymphocytes, 70% Blasts, 1% Myelocytes, 1% Metamyelocytes.

In this 83 year old female, the bone marrow pattern is MONONUCLEAR CELL INFILTRATION.

The bone marrow aspirate is hypercellular. Megakaryocytes are decreased.

Bone Marrow Differential: 65% Blasts, 1% Neutrophils/Bands, 18% Lymphocytes, 16% late Erythroid precursors.

The blasts are peroxidase positive and have abundant blue, vacuolated cytoplasm consistent with monoblasts. Positive NSE staining was seen in 90% of the cells.

Immunology: The blasts in the peripheral blood demonstrated a MYELOID phenotype.

INTERPRETATION:
Bone Marrow, aspirate: Acute Myeloid Leukemia, FAB M5a.

[Choose New Case]   [Next Case]

*Diagnostic Hem*
*A Pattern Appro*

Petrushka's Electronic Textbook

Table of Contents-Click on Blue Topic

Approach to Peripheral Blood
Blood Smear Preparation
Staining
Blood Smear Examination
Correlation with laboratory and clinical data

Peripheral Blood Patterns
Normal
Reactive Neutrophilia
Leukoerythroblastic
Abnormal Mononuclear Cell
Erythrocytosis
Thrombocytosis
Absolute Lymphocytosis
Thrombocytopenia
Eosinophilia
Monocytosis
Bi/Pancytopenia
Neutropenia/Leukopenia
Hypochromic, Microcytic
Macrocytic
Normochromic, Normocytic Anemia
Anemia with Anisocytosis
Leukemoid
Non-Specific Icon Bar

Petrushka's Electronic Textbook

Leukoerythroblastic

The leukoerythroblastic pattern is characterized by circulating NRBCs and immature myeloid precursors, associated with RBC anisopoikilocytosis. The WBC count can be normal or high. In most cases, this pattern is associated with anemia. The hemogram findings which accompany this pattern are the NRBC flag, immature granulocytes/band flag, and a high RDW.

Two major mechanisms, acting alone or in concert have been proposed to account for the peripheral blood changes characteristic of a leukoerythroblastic reaction:

- Infiltration of the bone marrow
- Extramedullary hematopoiesis

Morphologic Findings
Circulating NRBCs are abnormal except in the neonatal period.

A few NRBCs may be observed in the peripheral blood of term, healthy newborns up to five days of age. In premature infants, or those with hypoxic stress, the number of circulating NRBCs is higher.

The number of circulating NRBCs in leukoerythroblastic reactions varies, depending on the severity of the underlying pathology. All of the

FIG. 21

DECISION SUPPORT SYSTEM AND METHOD FOR DIAGNOSIS CONSULTATION IN LABORATORY HEMATOPATHOLOGY

BACKGROUND OF THE INVENTION

This invention relates to a system and method for conducting laboratory hematopathology diagnosis. By "hematopathology" is meant the medical science concerned with diseases of the blood and related tissues, including but not limited to spinal fluid, lymph nodes and bone marrow. Hematopathologists are generally considered to include such persons as hematologists, pathologists, immunologists and related scientists.

More specifically, the invention relates to a system and method for conducting hematopathology diagnosis based on results output from a hematology analyzer, flow cytometry (FCM) analyzer, and review of microscopic slides of bone marrow preparations. The invention provides a patterned approach to peripheral blood, FCM, and bone marrow analysis and serves to guide technologists and technicians through the complexities of hemogram interpretation, morphologic observations and complementary laboratory studies. Furthermore, the invention guides physicians in the interpretation of FCM studies and provides a means of generating multiparameter interpretive reports of hematology specimens. A logical mechanism of diagnostic reasoning is implemented through the use of a computer.

In medicine, diagnostic reasoning is the process of converting data obtained from examining a patient into names of diseases, which are of themselves conceptual medical entities that identify or explain the abnormalities in the observed evidence. In practice in a clinical setting, diagnostic reasoning often does not proceed in a direct continuous manner towards a precise disease identification, but is often interrupted by the performance of laboratory tests. Diagnostic consultation thus requires a strategy for evaluating evidence, recognizing patterns, ordering adjunctive tests and ultimately choosing the names of diagnostic entities.

A common screening test in clinical medicine is the hemogram or "complete blood count" (CBC). Analysis of hemogram data generated by sophisticated, modern hematology analyzers capable of automated "white blood cell" (WBC) differentials is routinely performed for most hematologic as well as non-hematologic disorders. Correct interpretation of the data will then indicate whether or not examination of the peripheral blood smear is necessary, and the hemogram findings together with the impression formed from scanning the blood smear, indicate when a manual WBC differential should be performed. Interpretation of the hemogram and peripheral blood smear findings leads to what is referred to conventionally as a diagnostic "station," an intermediate hypothesis during the diagnostic reasoning process. This "station" or "pattern" as referred to hereinafter, results in a narrow group of differential diagnoses and should provide an indication of which additional tests will confirm the diagnosis with minimum costs, delay and discomfort to the patient. Presently, conventional hematology analyzers, such as the commercially available Coulter® STKS hematology analyzer sold by Coulter Corporation of Miami, Fla., provide cell size distribution curves for red blood cells, WBC and platelets (PLT). The Coulter® STKS device analyzes the WBC populations by a combination of volume, conductivity and light scatter (VCS) measurements. An automated five-part WBC differential is then performed and suspect flags are generated for potential morphologic abnormalities by means of cluster analysis.

Typically, the correct interpretation of hematologic patterns, as well as the morphologic findings and the results of such tests as immunologic analysis of leukocytes by flow cytometry, is often difficult for laboratory personnel and physicians lacking specific training and expertise in the fields of hematology and hematopathology.

To facilitate such diagnosis, a number of computerized decision support programs have been developed to aid in the interpretation of hemogram findings. Of particular interest is that such programs have been developed with reference to the diagnosis of anemia. Often the approach employed by these systems include Bayesian probability as disclosed in "Decision-making systems (DMS) applied to hematology. diagnosis of 180 cases of anemia secondary to a variety of hematologic disorders" by Sultan C., Imbert M., Priolet G.; *Hematol Pathol* 1988; 2:221–8; statistical pattern recognition as disclosed in "The use of an expert system in the clinical laboratory as an aid in the diagnosis of anemia" by Blomberg D. J., Ladley J. L., Fattu J. M., Patrick E. A.; *AM J Clin Pathol* 1987; 87:608–13; multi-variate statistical analysis as disclosed in "Evaluation of BCDE, a microcomputer program to analyze automated blood counts and differentials" by Bates J. E., Bessman J. D.; *AM J Clin Pathol* 1987; 88:314–23, and rule-based production systems as disclosed in "An expert system for the interpretation of full blood counts and blood smears in a hematology laboratory" by Tolmie C. J., du Plessis J. P., Badenhorst P. N.; *Artif Intel Med* 1991; 3:271–85.

When such systems have been evaluated with a limited number of anemia cases, performance was judged satisfactory in about 84%–89% of the cases. While encouraging, the success numbers in terms of arriving at a correct diagnosis falls short of what is desired in an actual diagnostic environment.

Thus, in accordance with the invention, the problems of the prior art are avoided by employing a system and method which does not rely upon probability/statistics methodology to arrive at a differential diagnosis or interpretation of test results. Instead, a hierarchical classification of blood, immunophenotype and bone marrow patterns is established and a heuristic algorithm is applied to eliminate patterns based on data obtained from hematopathology analysis. For purposes of this disclosure, by "differential diagnosis" is meant a list of possible diagnoses or diagnostic possibilities. Further, by "interpretation of test results" is meant a diagnostic impression based on available data.

SUMMARY OF THE INVENTION

In one aspect, the invention is directed to a method of interpreting hematopathology test results to arrive at a diagnosis of a patient. As noted previously, hematopathology tests can include hematology, lymph node, bone marrow, flow cytometry, spinal fluid and other types of testing generally done to diagnose diseases of the blood and related tissues.

In accordance with its broadest aspect, the method includes retrieving data from at least one hematopathology test for a patient and storing the data in a database. The hematopathology test data is then compared to at least one set of a predetermined number of hematopathology patterns. Each of the hematopathology patterns corresponds to different patient conditions and they are arranged in a predetermined hierarchy. A comparison is done to determine which patterns match the hematopathology test data in the database. The matched patterns are thereafter displayed with recommendations corresponding to the matched patterns including either no additional testing (for example, if the patient condition is indicated to be normal) or a recommendation for one of a plurality of additional testing, the results of which are likely to lead to a diagnosis of the patient's condition.

As further refined, the method includes conducting any additional testing recommended, retrieving the data therefrom and storing it in the database with the hematopathology test data. A second comparison is then done with the original as well as the new data with the patterns, to determine which patterns match the test data in the database. At least one highest ranked pattern is identified to arrive at a differential diagnosis of the patient's condition.

As may be appreciated, in the ordinary course of diagnosis, the first hematopathology test conducted is a hematologyanalysis which may include a visual examination of a blood smear. This comparison may yield fairly conclusive results, may also lead to a suggestion of additional testing for a more definitive differential diagnosis or interpretation of the patient's test results. Thus, the additional testing recommended from the hematology test may include, but is not limited to flow cytometry or bone marrow testing. The flow cytometry or bone marrow data would then also be entered into the database and a follow-on comparison made of all the data to patterns, in the case of flow cytometry to a set of flow cytometry patterns, and in the case of bone marrow testing, to a set of bone marrow patterns, which would include as part of their identification any previous differential diagnosis resulting from the hematology testing.

Although hematology testing is indicated as typically being done first, it will be appreciated that either type of testing can be done as a stand-alone procedure, with the flow cytometry and bone marrow testing being more specific in results than the hematology testing. Although from the flow cytometry or bone marrow test results it is possible to arrive at a fairly specific diagnosis, it will also be generally recommended that a hematology test be done before reaching a conclusive diagnosis. In the case of flow cytometry it will be appreciated the multiple patterns each of equal and highest rank may be identified. Thus, this is why, for example, a hematology test may be indicated.

In another aspect, the invention is also directed to a system for interpreting hematopathology test results to arrive at a diagnosis of a patient. The system includes database storage for storing a database of test results from hematopathology test for specific patients. A knowledge base stores at least one set of a predetermined number of patterns corresponding to specific patient conditions, including at least a normal condition, and with the patterns arranged in a predetermined hierarchy. The knowledge base and an inference engine contain instructions for comparing the patterns to the database of test results for determining which patterns are matched. In the system of the invention, the knowledge base and inference engine are linked in the programming as implemented. A comparator serves to conduct the comparison from the tests for a specific patient with the patterns to determine which patterns are matched and which pattern is highest in the hierarchy. An input device serves to input data from the test results into the database and an output device serves to output the results of the comparison.

In accordance with a more specific aspect of the invention, there is provided a method of interpreting hematology results to arrive at a differential diagnosis for a patient with recommendations for additional diagnostic tests in the case of peripheral blood analysis. The method includes the steps of establishing a knowledge base of a predetermined number of exhaustive but not mutually exclusive hematology patterns. By the term "exhaustive number of patterns" is meant all of the most commonly occurring patterns, including a normal pattern, and one pattern which corresponds to abnormal conditions but not specific to any condition. The nonspecific pattern accounts for no more than about 5% of abnormal conditions showing what are typically nonsignificant abnormalities for diagnostic purposes. Further, by the term "knowledge base" is meant a set of defined patterns and programmed instructions for matching the patterns to input data for constructing a report from the matching.

One of the patterns in the knowledge base corresponds to a normal patient condition and each of the remaining patterns except one is representative of a corresponding differential diagnosis of specific conditions. The last predefined pattern in the peripheral blood module is designated "nonspecific" and, as previously noted, includes cases which do not meet the defined criteria for any of the other aforementioned patterns. Data is retrieved from at least a first hematology test for a specific patient. The data retrieved is then compared with the predetermined number of hematology patterns in the knowledge base to determine which hematology patterns match the data.

An input device is provided for inputting data from hematology tests for a specific patient. A comparing device serves to compare the data input by the input device with the predetermined number of hematology patterns in the database. An arranging or sorting device serves to arrange the hematology patterns which match the input data in a predetermined hierarchy. Since the patterns are not mutually exclusive, a predetermined hierarchy of the patterns is established.

Diagnostic reasoning proceeds according to the pattern matched which is highest in the hierarchy. A display displays the pattern highest in the hierarchy for indicating a differential diagnosis of the patient's condition. Computer program modules are implemented in the form of what are conventionally known as "if ... then" statements to generate recommendations for additional tests which may help to establish the final diagnosis of the patient's condition. These recommendations are displayed along with the peripheral blood pattern and the differential diagnosis.

In another aspect, the invention relates to a system for interpreting FCM results for generating an interpretation with a differential diagnosis in the case of FCM analysis. The system optionally includes database storage for both the results of the peripheral blood findings and the peripheral blood interpretation described above. The system also includes a knowledge base of a predetermined number of exhaustive but not mutually exclusive FCM patterns. Each pattern except one corresponds to a specific cell type (lineage). One pattern, designated "non-specific" corresponds to conditions which do not meet the definitions of the specific patterns because one or more FCM markers was not included in the panel of markers studied in a given patient specimen.

An input device is provided for inputting data from FCM tests for a specific patient. A comparing device serves to compare the data input by the input device with the predetermined number of hematology patterns in the knowledge base. An arranging and sorting device serves to arrange the FCM patterns which match the input data. Database programmed functions are provided to look up pericorresponding peripheral blood information stored in the database on the patient. Computer program modules are implemented in the form of "if . . . then" statements to use the input data and the data retrieved from the database in the interpretation of the findings. A display displays the FCM pattern(s) matched for indicating a differential diagnosis of the patient's condition and the remaining parts of the interpretation as generated by the computer program modules.

In another aspect, the invention relates to a system for aiding in the interpretation of bone marrow microscopic slides and generating a multiparameter report of the findings. As described above, the system optionally includes database storage for the peripheral blood findings and interpretation. The system also optionally includes database storage for the FCM findings and interpretation as well as the bone marrow findings and interpretation. In addition, the system also includes a knowledge base with a predetermined number of exhaustive but not mutually exclusive bone marrow patterns. Each pattern except one is representative of a corresponding differential diagnosis of specific conditions. One pattern, designated "non-specific" corresponds to conditions which do not meet the definition of the specific patterns.

An input device is provided for inputting data from observation of bone marrow microscopic slides by a physician (and a trained technologist, where appropriate). A comparing device serves to compare the data input by the input means with the predetermined number of bone marrow patterns in the knowledge base. An arranging and sorting device serves to arrange the bone marrow patterns which match the input data.

Since the patterns are not mutually exclusive, a predetermined hierarchy of the patterns is established. Diagnostic reasoning proceeds according to the pattern matched which is highest in the hierarchy. Database programmed functions are provided to look up any corresponding peripheral blood and FCM information stored on the patient. Computer program modules are implemented in the form of "if . . . then" statements to use the input data and the information retrieved from the database in the interpretation of the bone marrow findings. A display displays the appropriate peripheral blood information retrieved from the database, the highest bone marrow pattern matched in the hierarchy, the bone marrow morphologic findings input by the user, the FCM interpretation retrieved from the database (if FCM was performed on the a peripheral blood or bone marrow specimen from this patient) and the final diagnosis determined by the computer program modules.

In a more specific aspect, the system is implemented on a computer including a keyboard and a "direct access storage device" (DASD) connected thereto, such as a hard disk drive. In addition, the input devices can include an electrical interface directly connected to the computer and adapted for direct connection to a hematology analyzer, and optionally to a flow cytometry analyzer, for having the results of blood cell analysis, and flow cytometry analysis, conducted thereby input directly into the computer. The comparing devices are implemented in conventional "comparator/sorter" hardware components with associated instructions in such a computer.

BRIEF DESCRIPTION OF THE DRAWINGS

Having thus briefly described the invention, the same will become better understood from the following detailed discussion made with reference to the drawings wherein:

FIGS. 5, 6 and 7 are reproductions of actual screens from the hematology module to illustrate the user interface and the ability of the technologist to overrule the system recommendations based on observation of the peripheral blood smear at scanning magnification.

FIGS. 8, 9, 10, 11 and 12 are reproductions of actual screens from the hematology module to illustrate the operation of this module in a patient with acute leukemia.

FIGS. 13, 14 and 15 are screen displays illustrating the operation of the flow cytometry, i.e., FCM module of the invention.

FIGS. 16, 17, 18 and 19 are screen displays illustrating the operation of the bone marrow module of the invention in the case of a patient with acute myeloid leukemia.

FIGS. 20 and 21 illustrate actual screen displays from the electronic textbook associated with the hematology module, also described as "Professor Petrushka."

DETAILED DISCUSSION OF THE INVENTION

Initially, it is noted that throughout this specification, the terms "hematology" and "peripheral blood" findings are used interchangeably and mean the same thing. Further, the "hematology module" is interchangeably referred to as the "peripheral blood module," or as shown in the screen displays in the figures, as "Professor Petrushka" or "Petrushka." The flow cytometry or FCM module is interchangeably referred to as "Professor Fidelio" or "Fidelio," and the bone marrow module is interchangeably referred to as "Belmonte" or "Professor Belmonte."

Figure 1:
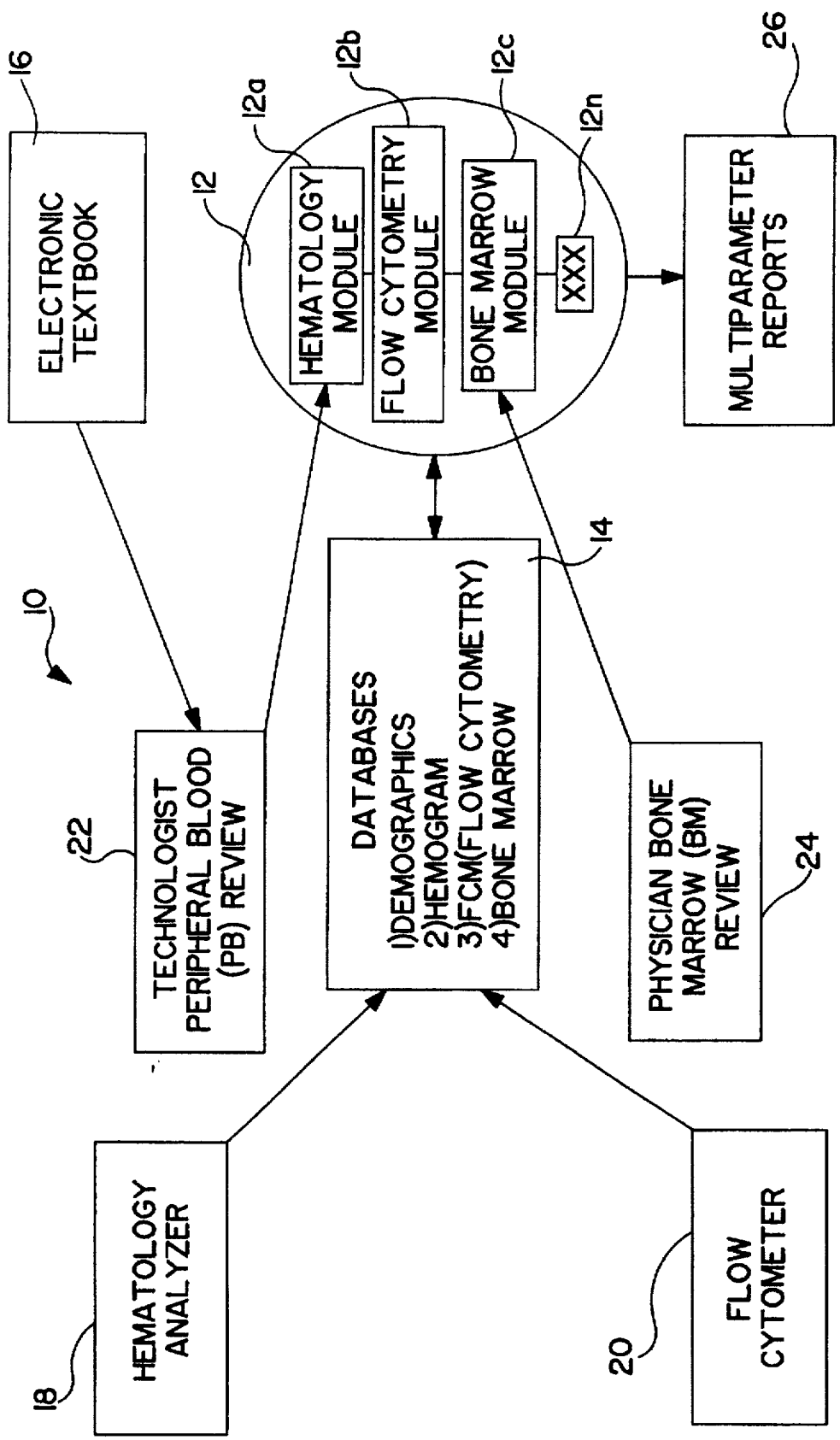
FIG. 1 is a block diagram illustrating the general system in accordance with the invention, including the interaction with a technician and/or a physician operating the system for conducting diagnosis.

The decision support system in accordance with the invention is generally shown in FIG. 1 and designated by the numeral 10. Included in the system 10 are a number of modules 12 made up of programmed instructions, as will become more clearly evident from the following discussion, which operate within a computer to process data to arrive at a differential diagnosis based on the results of hematopathology analysis.

In a preferred aspect, the invention as, presently contemplated includes three modules, a hematology module 12a, a flow cytometry module 12b and a bone marrow module 12c for processing the results of different tests on a patient. The modules 12a, 12b and 12c interact with databases 14 corresponding to each module and each module contains a knowledge base 13, as shown in FIG. 2, which illustrates the typical architecture of the decision support system of the invention, which includes a number of patterns each corresponding to a list of differential diagnoses.

Figure 2:
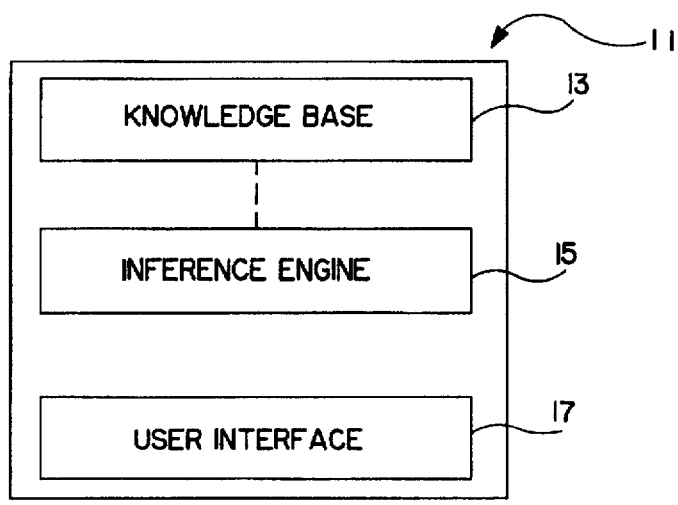
FIG. 2 is a block diagram of the typical architecture of a decision support system in accordance with the invention, including a knowledge base, inference engine, and a user interface.

In its least complex implementation, the system is implemented only with the hematology module 12a, the appropriate database 14 and the corresponding knowledge base 13, inference engine 15, and a user interface 17, as shown in FIG. 2, which for interpretation of the results of hematology analyzer 18 as described hereafter.

For hematology analysis the patterns shown in the following Table I are stored in the knowledge base 13:

TABLE I

| PERIPHERAL BLOOD PATTERNS | |
|---|---|
| 1. Normal | 10. Monocytosis |
| 2. Reactive Neutrophilia | 11. Bi-Pancytopenia |
| 3. Leukoerythroblastic | 12. Leukopenia |
| 4. Abnormal Mononuclear Cell | 13. Hypochromic and/or Microcytic |
| 5. Erythrocytosis | 14. Macrocytic |
| 6. Thrombocytosis | 15. Normochromic, Normocytic Anemia |
| 7. Absolute Lymphocytosis | 16. Anemia with Anisocytosis |
| 8. Thrombocytopenia | 17. Leukemoid |
| 9. Eosinophilia | 18. Non-specific |

Figure 3:
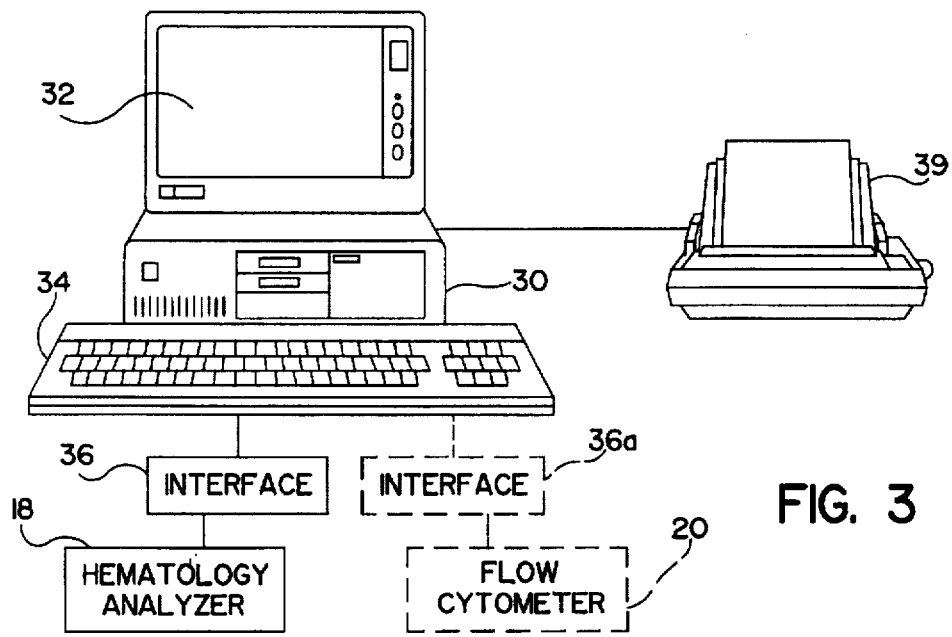
FIG. 3 is a general block diagram illustrating a typical computer system on which the invention can be implemented.

As shown in FIG. 3, a computer 30 of the system 10 is typically connected through a hardware interface 36 to a hematology analyzer 18. As also shown in FIG. 3, it is possible to implement the invention with more than a hematology analyzer 18 in a complete hematopathology diagnostic system. For example, it is also possible to connect a flow cytometry analyzer 20 through interface 36a to computer 30. In this embodiment the flow cytometry module (FCM) will contain the corresponding knowledge base 13, inference engine 15, and user interface 17 as shown in FIG. 2, and the database 14 of FIG. 1 will contain a table of data appropriate for FCM data as shown in Appendix 3, and the knowledge base 13 contains flow cytometry patterns as shown in Table II below. Similarly, the system can also include a bone marrow module 12c, with the bone marrow module 12c patterns employed in a similar manner as discussed hereafter and shown in Table III following Table II below.

TABLE II

| FLOW CYTOMETRY IMMUNOPHENOTYPING PATTERNS | |
|---|---|
| 1. Stem Cell | 6. Immature T-cell |
| 2. Myeloid | 7. Mature B-cell |
| 3. Erythroid | 8. Mature T-cell |
| 4. Megakaryocytic | 9. Plasma cell |
| 5. Immature B-cell | 10. Non-specific |

TABLE III

| BONE MARROW PATTERNS | |
|---|---|
| 1. Normocellular | 7. Mononuclear cell infiltration |
| 2. Hypocellular | 8. Foreign cell infiltration |
| 3. Erythroid predominance/hyperplasia | 9. Granulomatous |
| 4. Hypercellular, myeloid | 10. Bi-hyperplasia |
| 5. Megakaryocytic hyperplasia predominance/hyperplasia | 11. Non-specific |
| 6. Lymphocytosis/plasmacytosis | |

Typically, the system 10, as shown in FIG. 3, will consist of a computer 30 connected to an input device such as a keyboard 34, and an output device such as a display 32. The computer 30 can also be directly connected through the electrical interface 36 to a hematology analyzer 18 through which the results of a test conducted therein can be directly input into the computer. Such a hematologyanalyzer 18 can be, for example, a Coulter® STKS hematology analyzer, such as sold by Coulter Corporation of Miami, Fla., which is presently commercially available and well known to those of ordinary skill in the art.

Figure 4:
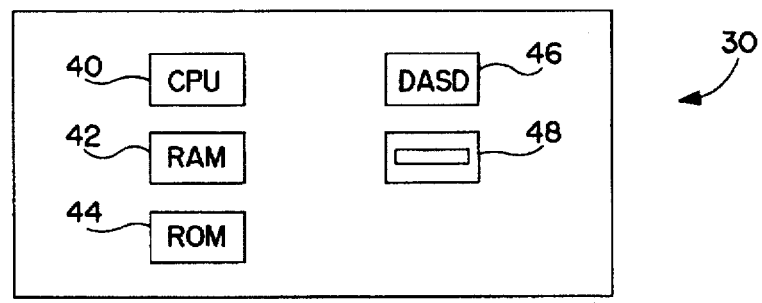
FIG. 4 is a block diagram of a typical computer of the type shown in FIG. 3, illustrating the various components thereof.

The specifics of the computer 30 on which the system 10 is implemented and which is conventional, are more clearly shown in FIG. 4 which shows the computer 30 including a conventionally arranged central processing unit 40 including "read only memory" (ROM) 44 which includes, for example, the necessary basic input/output system instructions such as employed in an IBM® personal computer under the name BIOS. "random access memory" (RAM) 42 serves to store data and instruction from a keyboard or other input device, as well as from a "direct access storage device" (DASD) 46, such as a hard disk drive, or a floppy disk drive 48.

The input from the analyzer 18 will include WBC, RBC and platelet (PLT) population flags and suspect flags for morphologic abnormalities which should be looked for on the peripheral blood smear.

One suspect flag is for blasts which are known to those of ordinary skill in the art as being the most immature white blood cells. Blasts are found circulating in the blood in large numbers only in serious malignant conditions such as acute leukemia and related disorders. Therefore, a suspect blast flag means that the corresponding blood smear should be carefully reviewed. Other suspect flags are for: 1) immature granulocytes/bands (another type of immature white blood cells found in infections); 2) variant lymphocytes (an "atypical" circulating lymphocyte found in viral infections such as infectious mononucleosis); and 3) red blood cell (RBC) and platelet abnormalities such as RBC fragmentation, RBC agglutination, circulating nucleated RBCs (NRBCs—which are normally found only in the bone marrow) and platelet clumps (platelets are the cellular elements which help the blood to clot).

In a preferred aspect, the system is implemented on an IBM® compatible computer operating under Microsoft Windows™ 3.1 software, available from Microsoft Corporation of Redmond, Wash., to provide an appropriate user interface and interaction for a technician or physician. The programming of the modules 12a, 12b and 12c can be implemented in a conventional manner once knowledge of the invention is known from the description herein, for example, by the use of the commercially available Turbo Pascal™ for Windows™ software, and the programming of databases 14 can be implemented in a conventional manner with the commercially available Borland Paradox™ Engine 3.01, software, all of which are well known to those of ordinary skill in the art.

With respect to the database 14, the structure of each table in the database in the preferred implementation is shown in Appendices 1, 2, 3, and 4, shown at the end of this specification, for database components 1) patient demographics; 2) hemogram/peripheral blood data; 3) FCM data; and 4) bone marrow data; respectively.

Each module 12a, 12b, ... 12n includes a knowledge base 13 as defined previously. The knowledge base 13 of each of the decision support software modules 12a, 12b, ... 12n, for example, the hematology module 12a, contains definitions of each of the patterns such that more than one pattern can coexist in the same case. For example, in acute leukemia, a thrombocytopenia pattern and/or normochromic, normocytic anemia pattern maybe present in addition to an abnormal mononuclear cell pattern. Since the goal is to arrive at a single dominant pattern, hierarchical classification of the patterns is arranged based upon the principles that, if WBC abnormalities are present, associated RBC and platelet abnormalities tend to be secondary to the WBC abnormalities, and the dominant pattern is the one that suggests a more specific, i.e., shorter, list of differential diagnoses. The latter rule is inferred from a commonly accepted heuristic criterion of diagnostic reasoning known as "Occam's razor" which states that the least complex of competing hypotheses is more likely to depict reality than the more complex hypotheses.

Thus, in implementation the hematology analyzer 18 values are displayed on the display 32, for example, a flat-panel display or a "cathode ray tube" (CRT) display, and referred to by the user of the device, e.g., a technician generally designated as box 22 of FIG. 1. Illustrative of what is displayed and referred to by the technician 22 on the display 32 are FIGS. 5 and 8. FIG. 5 illustrates the first screen displayed by the hematology module 12a which shows the hemogram parameters received from the hematology analyzer, including a suspect flag for NRBCs. FIG. 8 illustrates the hemogram findings received from the hematology analyzer including a suspect flag for blasts which are immature white blood cells that are only found circulating in the blood in large numbers when the diagnosis is acute leukemia or a related condition.

The hematology module 12a then automatically calculates a preliminary pattern based on the hemogram findings when the last analyzer parameter is received and the age and sex of the patient are known. The preliminary pattern is then displayed in a scrollable window of the display 32 and the hematology module 12a recommends a specific approach to the review of the peripheral blood smear based on the patterns that were present in the conflict set after the first pass through the data. This is illustrated by FIGS. 6 and 9.

FIG. 6 illustrates the second screen generated by hematology module 12a in which the system has indicated the NRBC suspect flag by automatically setting the check box "NRBCs." In this illustration the system has made a preliminary interpretation (based upon hemogram findings alone) which is then displayed in a scrollable field shown in the upper half of FIG. 6.

Because of the NRBC suspect flag, the system has automatically set the "accept automated differential?" radio button to "No" and has indicated a morphologic review of white blood cells is necessary by setting the WBC check box. In FIG. 9 the preliminary indication generated by hematology module 12a includes a recommendation for reviewing RBC and WBC morphology and a manual WBC differential. The technologist 22 has agreed with the system recommendations after viewing the peripheral blood smear at scanning magnification.

As shown in FIG. 1, the technologist or user as illustrated by block 22 has complete control and has access to an electronic textbook 16 which allows access to didactic information as illustrated by FIGS. 20 and 21. The electronic textbook can be implemented, for example, in the commercially available electronic document design and publishing software product called Guide™, which is available from Infoaccess, Inc. of Belleview, Wash. In FIG. 20 there is shown the "Table of Contents" window of the textbook. FIG. 21 illustrates a screen from within the textbook in the chapter on the "Leukoerythroblastic" pattern. The text is displayed in "Hypertext" format. The boldface text with the arrow symbol is displayed in blue on the computer terminal indicating that the heading can be expanded to show more information. In FIG. 21, the user or technician 22 has clicked on the underlined text "except in the neonatal period" which brings up a comment box with further information about NRBCs in the newborn infants.

Thus, for example, in a case where the hematology analyzer 18 in FIGS. 1 and 2 reports a false, positive flag for NRBCs on the basis of the NRBC flag, for example, as illustrated in FIG. 5, the hematology module 12a would calculate and recommend a manual WBC differential for two reasons: 1) the WBC count may need to be adjusted if a significant number of NRBCs were counted as leukocytes; and 2) the presence of circulating NRBCs may be associated with immature myeloid precursors in the peripheral blood. If the technologist 22, after scanning the peripheral blood smear, concludes that there are no circulating NRBCs, the technologist 22 notes that fact by un-highlighting the NRBC check box on the system. If the NRBC flag is the only feature which is causing the hematology module 12a to recommend a manual WBC differential, the system responds by withdrawing its recommendation for a manual differential. This is illustrated by FIG. 7 which is the same screen as FIG. 6 showing changes after interaction with the technologist 22.

The technologist 22, after scanning the peripheral blood smear, has performed two functions as follows: 1) no NRBCs were visible on the peripheral blood smear (i.e., the analyzer suspect flag for NRBCs was a false positive). Therefore, the technologist 22 has unchecked the NRBC check box by clicking on the box. The system responded by automatically resetting the "Accept Automated Differential?" radio button to "Yes" since the only hemogram finding which supported a manual WBC differential was the NRBC suspect flag; and 2) the technologist 22 has also unchecked the WBC check box indicating that WBC morphology was normal at scanning magnification.

Likewise, the system 10 may recommend additional types of analysis such as, for example, a flow cytometry test from a flow cytometer 20 in which a flow cytometry module 12b comes into play with its own set of patterns (Table II) stored within the corresponding knowledge base 13 to be combined in a hierarchical manner to compliment the pattern operated on by the hematology module 12a. As may be appreciated, it is also possible to add additional tests as illustrated by FIG. 12, such as bone marrow testing which results are processed by a bone marrow module 12c with its own patterns (Table III), the results of the test being reviewed by a physician, generally shown as box 24 in FIG. 1, as well as other tests as generally shown by the box labeled "XXX" and identified as 12n in FIG. 1. Such tests can include, for example, lymph node testing which results, as in the case with bone marrow testing, are all manually input through the keyboard 34 of FIG. 2.

In FIG. 12 there is illustrated the final interpretation and recommendation screen of the hematology blood module 12a, known as "Professor Petrushka." The highest pattern matched in the hierarchy "abnormal mononuclear cell pattern" is displayed in a scrollable field along with: 1) the specific findings in the peripheral blood; 2) the differential diagnosis (which, in this case, consists of only one diagnosis); and 3) a statement as to the specific diagnosis "acute myeloid leukemia" suggested by the finding "auer rods present." The recommendations for follow-up tests in this case are shown as including a bone marrow aspirate/ biopsy, cytochemical stains, and immunophenotyping by flow cytometry.

The interaction between the modules 12a, 12b and 12c results in a multi-parameter report 26 which results in a recommended diagnosis. In the case of the technologist 22 as well as the physician 24, it is also possible to access the electronic textbook 16 which explains the different conditions or patterns indicated by the hematology module 12a, flow cytometry module 12b and/or bone marrow module 12c to allow greater understanding of the diagnostic process as illustrated by FIGS. 20 and 21. The electronic textbook, as in the case with the database, would also be stored in DASD 46 with the knowledge base 13 and the modules 12a, 12b, 12c, . . . 12n.

The electronic textbook 16 can be constructed from information obtained from the texts: "*Wintrobe Clinical Hematology,*" 9th Edition, G. Richard Lee, Thomas C. Bithell, John Foerster, John W. Athens and John N. Lukens (editors), Lea & Febiger, Philadelphia, 1993; "*Hematology of Infancy and Childhood,*" 4th Edition, David G. Nathan and Frank A. Oski (editors), W. B. Saunders, Philadelphia, 1992; and "*Blood Textbook of Hematology,*" James H. Jandl, Little, Brown and Company, Boston 1987. As previously noted, the substance of these texts can be implemented into the electronics textbook 16 in a conventional manner by those of ordinary skill in the art, with, for example, the electronic document design and publishing software available under the name Guide™ from InfoAccess, Inc., of Bellevue, Wash.

Figure 22:
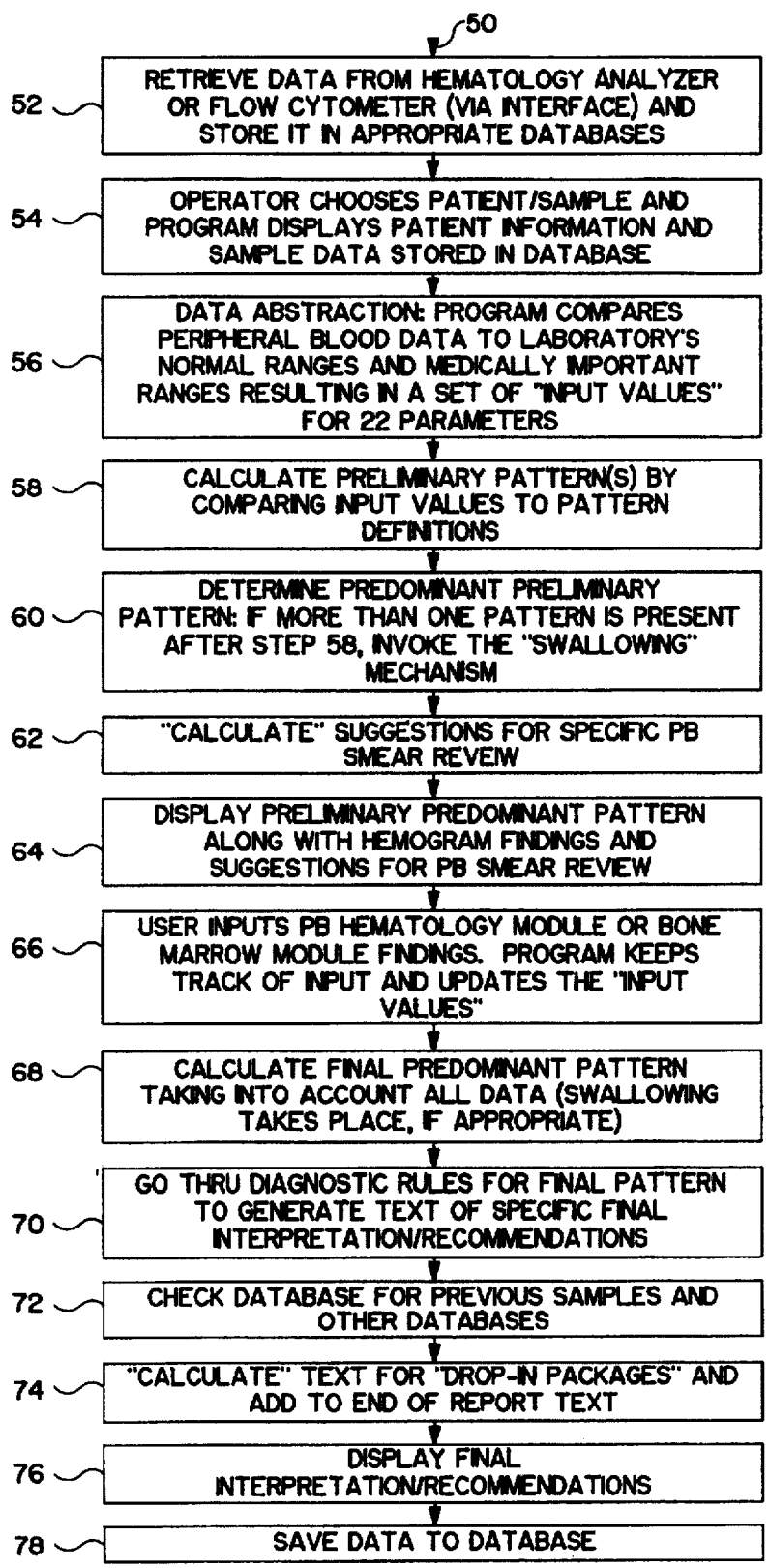
FIG. 22 is a block diagram illustrating the steps taken in conducting the method in accordance with the invention.

Having generally described the system and environment of the invention, FIG. 22 more clearly illustrates the method of the invention in a flow chart 50.

In its present implementation, the system in accordance of the invention consists of three knowledge based modules, i.e., a hematology module 12a, a flow cytometry module 12b and a bone marrow module 12c, along with associated databases 14, an electronic textbook 16 with digitized images of, for example, abnormal blood cells, and in addition, educational materials available from Coulter Corporation of Miami, Fla. under the name "*Coulter VCS Technology Case Studies,*" volumes 1 and 2, 1992, showing case studies which are entered in the same format as the information from the previously mentioned textbooks. The modules 12a, 12b and 12c serve to interpret data from a hematology blood analyzer such as a Coulter® STKS analyzer, a flow cytometry analyzer for interpretation of flow cytometry data, i.e., immunophenotyping and DNA content analysis, such as a Coulter® EPICS series flow cytometer, and bone marrow analysis of bone marrow morphology.

As shown in FIG. 22, there are fourteen steps implemented by the system modules 12a, 12b and 12c. Only the hematology module 12a follows all fourteen steps with the calculation of a preliminary pattern. The flow cytometry module 12b goes directly from step 56 to step 68 and displays the final interpretation without user interaction. The bone marrow module 12c obtains the necessary peripheral blood data from the database 14 in step 54 and displays it along with suggestions for additional tests, such as, flow cytometry, i.e., FCM, special stains, cytogenetics, etc., based on the peripheral blood, i.e., PB, pattern. Then the bone marrow module goes directly from step 54 to step 66, performing the functions of step 56, i.e., data abstraction as illustrated hereafter, after all the data is collected, i.e., between steps 66 and 68. All three modules 12a, 12b and 12c, have incorporated therein the calculations of steps 56, 58 and 60, except that all of the data is taken into consideration at that point. The term "data abstraction" refers to the process of comparing the raw data to the laboratory's normal ranges and the medically important values that have been obtained from, for example, the texts employed to build the electronic textbook 16, resulting in a series of input values to step 58.

As previously discussed, knowledge representations in all three systems are based on defined patterns which serve as intermediate hypotheses in the diagnostic reasoning process. Within each pattern, there are additional "rules" obtained from standard textbooks of hematology as discussed previously with reference to establishing the electronic textbook 16, which are followed to generate the text to the final interpretations and recommendations. This type of rule, an "if . . . then" statement, e.g., "if observation 1 [and/or observation 2] . . . then conclusion," is well known to those of ordinary skill in the art. Specific examples of how these "rules" can be implemented to generate a text report are illustrated in Appendices 5, 6 and 7, which contain example code, and are shown at the end of this specification for the hematology module 12a, flow cytometry module 12b and bone marrow module 12c, respectively.

It can be appreciated that an important feature which distinguishes the present invention from other systems, is the method of knowledge representation implemented by the system. In accordance with the invention there is first established a list of predetermined patterns, i.e., the names of each of the patterns. Then, the knowledge about the patterns is fixed by answering the following three questions about each pattern:

1) what minimum set of input data must be present to establish a positive match with the pattern under consideration?
2) is there any single piece of input data, or combination of input data, which, when present, rules out, i.e., excludes, that pattern from further consideration? and
3) what other patterns on the predetermined list are lower on the hierarchy than the pattern being considered, i.e., what other patterns can be "swallowed" (hereafter referred to as "swallowing" or "swallowing mechanism" which refers to the arrangement of patterns on the basis of which patterns predominate others) by the pattern under consideration?

These questions are answered in the practice of the invention, as shown from the tables, and the description of the program steps of FIG. 22 as discussed hereafter.

A description of the flow diagram 50 of FIG. 22 follows.

At step 52, a hematology workstation, for example, consisting of a IBM®-compatible computer with associated peripherals as shown in FIG. 3 and the software including modules 12a, 12b, 12c, . . . 12n is interfaced to a hematology analyzer 18 and a flow cytometer 20, for example, such as the commercially available Coulter® STKS hematology analyzer and commercially available Coulter® EPICS Series flow cytometer, both available from Coulter Corporation of Miami, Fla. An interface 36 directly connects the hematology analyzer 18 to the computer 30. As data is transmitted from the hematology analyzer 18, alternatively from a flow cytometer 20, or input by hand through a keyboard 34 as shown in FIG. 13 which illustrates the screen dialog box for manually inputting the results of the flow cytometer 20 into the flow cytometry module (FCM) 12b, it is stored in a set of relational databases. As previously noted, such databases can be implemented through programming created through the use of the commercially available Borland Paradox™ Engine software program (see Appendices 1–4 showing example code). In addition to the patient's medical record number, age, sex and date of birth, the demographics database has fields for clinical history and other pertinent laboratory tests related to hematologic disease. The clinical information is entered into the system manually and is stored in the demographics database (see Appendix 1).

The hemogram/peripheral blood (PB) database stores all of the numerical parameters normally transmitted from a hematology analyzer 18, as well as the suspect flags for morphologic abnormalities in the RBC, WBC, and platelet populations transmitted by the hematologyanalyzer (appendix 2). Wherever, in Appendices 1 through 4, the field type is referred to as "alphanumeric" (coded bitmap), this means that the data is coded in a string of characters.

For example, in Appendix 2, item 29, "suspect flags" is listed as field type alphanumeric (coded bitmap). There are 8 suspect flags transmitted by the hematology analyzer which are stored in this field. These flags are: 1) blasts; 2) immature granulocytes/bands; 3) variant lymphs; 4) NRBCs; 5) dimorphic RBC; 6) micro RBCs/RBC fragments; 7) RBC agglutination; and 8) platelet clumps (see FIG. 5). Field 29 of the hemogram database, "suspect flags," is a string of 8 characters, conventionally numbered characters 0 through character 7 using the nomenclature of so-called "null-terminated strings" known to individuals of ordinary skill in the field of computer programming. The result of the suspect flag "blasts," i.e., present or absent, is stored in character 0 of the string as a "0" (absent) or "1" (present); the result of the flag "immature granulocytes/ bands," i.e., "absent," "flag type 1," or "flag type 2," is stored in character 1 of the string as a "0" (absent), "1" (Flag type 1) or "2" (flag type 2). The remaining flags can only be present or absent, and are stored in the subsequent characters of the string exactly as for the "blasts" flag. Therefore, if the hematology analyzer transmits only a "variant lymph" flag and all of the other flags are negative, the character string "00100000" is stored in field 29 "suspect flags."

In step 54, the operator chooses a case, i.e., a patient/ sample, and the system displays data retrieved from the database 14. The hematology module 12a displays the hemogram findings, the flow cytometry module 12b displays all of the flow cytometry data.

FIG. 14 shows the screen from the flow cytometry module 12b displaying the flow cytometry data on a lymph node biopsy in a patient with "chronic lymphocytic leukemia" (CLL). The (dta (displayed on the left) were manually input by the user as fluorescence intensity. FIG. 15 shows the screen from the flow cytometry module 12c showing the interpretation of flow cytometry testing performed on a peripheral blood specimen from a patient with "acute lymphoblastic leukemia" (ALL). The flow cytometry data was input by the user as a percentage of positive cells.

The bone marrow module 12c looks up the patient's blood findings in the hemogram/PB database and displays them along with recommendations for the bone marrow which are triggered by the PB pattern. FIG. 16 shows the first screen in the bone marrow module 12c when the user entered the specimen identification number into a dialog box (not shown), the system 10 responded by looking up the peripheral blood information on this patient saved in the database 14. The peripheral blood findings are displayed along with recommendations as to how to approach the bone marrow examination. In this case there are reminders for the additional tests which need to be performed on the bone marrow.

The type of program to be implemented for retrieving such information from a database and displaying such information on the screen will be readily apparent to those of ordinary skill in the art of computer programming based on this description.

In step 56 all of the modules 12a–12c go through a process of data abstraction. Specifically, as previously noted, "data abstraction" refers to the process of comparing the raw data, i.e. the instrument parameters, to the normal ranges for these parameters set by the laboratory, and to the medically important ranges for these parameters which are obtained from the standard hematology textbooks such as have been identified with reference to the electronic textbook 16. The concept of "data abstraction" and "heuristic classification" are well known, as is apparent from the text "Heuristic Classification," Clancey, W. J., "Artificial Intelligence," 1985; 27:289–350. The comparison between the instrument parameters and the normal and medically important ranges results in a set of "input values" to the computer program, i.e., the inference engine 15 designed as modules 12a, 12b, 12c, . . . 12n. The input parameters for the peripheral blood module 12a, are listed in Table IV below.

TABLE IV

PERIPHERAL BLOOD INPUT PARAMETERS

| | | |
|---|---|---|
| 1. Age | | 1a = 0–1 (infant) 1b = 2–13 (child) 1c = 14–35 (young adult) 1d = 36–49 (adult) 1e = 50–69 (middle age) 1f = greater than 69 (elderly) |
| 2. Sex | | 2a = male 2b = female |
| | Actual numeric values for parameters 3–13 set by hospital laboratory normal ranges and medically important ranges | |
| 3. Hgb | | 3a = severe anemia 3b = moderate anemia 3c = mild anemia 3d = normal 3e = mild polycythemia 3f = severe polycythemia |
| 4. MCV | | 4a = microcytosis 4b = normocytic 4c = macrocytosis |
| 5. MCH | | 5a = hypochromic 5b = normochromic |
| 6. RDW | | a = normal 6b = mild anisopoikilocytosis 6c = marked anisopoikilocytosis |
| 7. PLT | | 7a = thrombocytopenia 7b = normal 7c = thrombocytosis |
| 8. WBC | | 8a = severe leukopenia 8b = mild leukopenia 8c = normal 8d = mild leukocytosis 8e = severe leukocytosis |
| 9. Neut | | 9a = granulocytopenia 9b = normal 9c = granulocytosis |
| 10. Lymph | | 10a = lymphocytopenia 10b = normal 10c = mild lyphocytosis 10d = severe lymphocytosis |
| 11. Mono | | 11a = normal 11b = absolute monocytosis |
| 12. Eos | | 12a = normal 12b = eosinophilia |
| 13. Baso | | 13a = normal 13b = basophilia |
| 14. WBC Population Flag | | a = normal b = abnormal |
| 15. RBC Population Flag | | a = normal b = abnormal |
| 16. PLT Population Flag | | a = normal b = abnormal |
| 17. Suspect Blasts Flag | | a = present b = absent |
| 18. Suspect Immature Granulocytes/ Bands Flag | | a = present b = absent |
| 19. Variant Lymphs Flag | | a = present b = absent |
| 20. NRBCs Flag | | a = present b = absent |
| 21. MicroRBC/ Fragments Flag | | a = present b = absent |
| 22. *Platelet Clumps Flag | | a = present b = absent |
| 23. Dimorphic RBC Flag | | a = present b = absent |
| 24. *RBC Agglutination | | a = present b = absent |
| 25. *MCHC | | Normal vs Increased |

*= Used only for setting a check box on the screen or displaying text. Not considered by the program.

For the hematology module 12a there are up to 25 parameters, of which 22 are used by the program in step 58 (see Table IV). For example, for parameter #3 (Hgb), the results of "data abstraction" are as follows, depending on the laboratory's normal range: 3a=severe anemia, 3b=moderate anemia, 3c=mild anemia, and 3d=normal Hgb, 3e=mild polycythemia, 3f=severe polycythemia. For the flow cytometry module 12b there are thirty-seven immunologic markers and several DNA-analysis parameters such as cell size, DNA index and percentage of cells in S-phase which get abstracted and translated into "input values" to the program. These parameters are listed in Table V below.

TABLE V

FLOW CYTOMETRY INPUT PARAMETERS

| | |
|---|---|
| 1. Age | 24. CD45 |
| 2. Sex | 25. CD56 |
| 3. Specimen Type | 26. CD57 |
| 4. CD1a | 27. CD61 |
| 5. CD2 | 28. CD71 |
| 6. CD3 | 29. Kappa |
| 7. CD4 | 30. Lambda |
| 8. CD5 | 31. Ia (HLA-DR) |
| 9. CD7 | 32. Glycophorin A |
| 10. CD8 | 33. Cytoplasmic Kappa |
| 11. CD10 | 34. Cytoplasmic Lambda |
| 12. CD11c | 35. Cytoplasmic Mu |
| 13. CD13 | 36. Cytoplasmic CD3 |
| 14. MY4 (CD14) | 37. Cytoplasmic CD22 |
| 15. Mo2 (CD14) | 38. Tdt |
| 16. CD16 | 39. Myeloperoxidase (by cytochemistry) |
| 17. CD19 | 40. Myeloperoxidase (by monoclonal antibody) |
| 18. CD20 | 41. Cell Size [Small, Medium, Large, Variable, Bimodal] |
| 19. CD22 | 42. DNA-Index |
| 20. CD25 | 43. % S-phase |
| 21. CD33 | 44. % Abnormal Cells |
| 22. CD34 | 45. % Blasts or Promyelocytes Present |
| 23. CD41 | 46. Peripheral blood and clinical findings [from database 14] |

For item 3, Specimen Types are: PB = Peripheral Blood, BM = Bone Marrow, LN = Lymph Node, SP = Spleen, FL = Fluid, EN = Extranodal
Items 4–40 are expressed either: (1) in percent positive (>30 = positive); or, (2) by fluorescence intensity [–/+/++/+++] (except item 39)
During Data Abstraction (Step 56) Items 4–40 are designated: POSITIVE (% > 30 or + or ++ or +++), NEGATIVE(% < = 30 or –) or NOT DONE.

For the bone marrow module 12c, the results of the user's input for the bone marrow differential and the qualitative/ quantitative features from the aspirate and biopsy (cellularity, presence of abnormal cells, results of special stains, etc.) make up the "input values." A complete listing of the bone marrow input parameters is found in Table VI below.

TABLE VI

BONE MARROW INPUT PARAMETERS

1. Age
2. Sex
3. Specimen(s) [Aspirate/Biopsy/Touch Prep]
4. Peripheral Blood Findings [from database 14]
5. Spicules [Present/Absent]
6. Megakaryocytes [Normal/Decreased/Increased]
7. Bone Marrow Cellularity [%]
8. Abnormal Mononuclear Cells/Foreign Cells [Present/Absent/Type]
9. Bone Marrow Differential
10. Erythroid Karryorhexis [Present/Absent]
11. Hypogranulation [Present/Absent]
12. Abnormal Eosinophils [Present/Absent]
13. Nuclear/Cytoplasmic Asynchrony [Absent/Myeloid/Erythroid/ Myeloid and Erythroid]
14. Giant Precursors [Absent/Myeloid/Erythroid/Myeloid and Erythroid]
15. Cytoplasmic Vacuoles [Absent/Myeloid/Erythroid/Myeloid and Erythroid]
16. Organisms
17. Bony Trabeculae [Normal/Thick/Thin]
18. Collagen Fibrosis [Present/Absent]

TABLE VI-continued

BONE MARROW INPUT PARAMETERS

19. Pattern of Lymphocyte/Plasma Cell Infiltration [Diffuse/Nodular/Paratrabecular]
20. Granulomas [Present/Absent]
21 Iron Storage [Normal/Decreased/Increased]
22. Iron Incorporation [Normal/Decreased/Increased]
23. Ring Sideroblasts [%]
24. Peroxidase Stain [Positive/Negative]
25. Non-Specific Esterase Stain [% positive]
26. PAS Stain [Positive/Negative]
27. TRAP Stain [Positive/Negative]
28. Reticulin Stain [Negative/1+/2+/3+]
29. Flow Cytometry Findings [from database 14]

For the hematology module 12a, the program in step 58 works as follows: The first 17 peripheral blood patterns, i.e., all of the patterns except for the "non-specific" pattern, are assembled into a set. At this point, at the start of the program, the set "patterns matched" indicated in computer programming by elements between square brackets contains 17 values as follows [1 2 3 4 5 6 7 8 9 10 11 12 13 14 15 16 17]. The input values from step 56 are then compared to the pattern definitions for each of the 17 patterns beginning with pattern 1 and continuing sequentially until pattern 17. The pattern definitions for the hematology patterns shown in Table VII as follows.

TABLE VII

PERIPHERAL BLOOD PATTERN DEFINITIONS

| Pattern | Definition |
|---|---|
| 1. Normal | No abnormality; No STKS suspect flags |
| 2. Reactive Neutrophilia | Increased WBC Count (<50,000) and increased neutrophils |
| 3. Leukoerythroblastic | NRBC flag, Immature gran/band flag, Increased RDW |
| 4. Abnormal mononuclear cell | Blast flag or variant lymphocyte flag |
| 5. Erythrocytosis | Increased Hgb |
| 6. Thrombocytosis | Increased platelet count |
| 7. Absolute lymphocytosis | Increased lymphocyte count and lymphocytes>=35% |
| 8. Thrombocytopenia | Decreased platelet count |
| 9. Eosinophila | Increased eosinophil count |
| 10. Monocytosis | Increased monocyte count and monocytes>=15% |
| 11. Bi-pancytopenia | Decreased (two or more) of: Hgb, WBC count, Platelet count |
| 12. Leukopenia | Decreased WBC count or Decreased Neutrophil count |
| 13. Hypochromic and/or microcytic | Decreased MCH or Decreased MCV |
| 14. Macrocytosis | Increased MCV |
| 15. Normochrmic, normocytic anemia | Decreased Hgb, normal MCH, normal MCV |
| 16. Anemia with anisocytosis | Decreased Hgb, Increased RDW |
| 17. Leukemoid | Increased WBC count (>50,000), Immature gran/band flag, Neut>=65% |
| 18. Non-specific | Anything which does not meet definitions 1–17 |

The pattern definitions are expressed within the program as simple "if . . . then" statements well known to those of ordinary skill in the art. The system in accordance with the invention eliminates those patterns whose definitions are not met. Therefore, the "if . . . then" statements are of the form, "if the pattern definition for pattern x is not met, then eliminate pattern x from the set patterns matched." For example, it can be seen from Table IV above that the input value "7c" means thrombocytosis which is the medical term for an increased platelet count. It can also be seen from previously set forth Table VII above that the only parameter in the definition for pattern 6 (thrombocytosis) is an increased platelet count, i.e., thrombocytosis. In English sentence structure, the "if . . . then" statement for pattern 6 is therefore, "if the input value 7 is not 7c then remove pattern 6 from list of patterns matched." As mentioned above, each pattern from 1 to 17 is evaluated in exactly this manner according to its own definition.

The FCM module 12b and the bone marrow module 12c performpattern matching in an exactly analogous manner but they do so in step 68 (final pattern) only. There is no preliminary pattern for the FCM and bone marrow modules 12b and 12c. The pattern definitions for the FCM module are shown in Table VIII below and the possible input parameters to step for the FCM module 12b are listed in Table V above.

VIII
FLOW CYTOMETRY PATTERN DEFINITIONS

| Pattern | Definition |
| --- | --- |
| 1. Stem Cell | Positive for Tdt or CD34 |
| 2. Myeloid | Positive for Myeloperoxidase or CD13 or CD33 |
| 3. Erythroid | Positive for Glycophorin A |
| 4. Megakaryocytic | Positive for CD41 or CD61 |
| 5. Immature B-cell | Positive for (Tdt or CD34) and (CD19, CD22, cCD22 or cmu) |
| 6. Immature T-cell | Positive for (Tdt or CD34) and (CD7 or cCD3) |
| 7. Mature B-cell | Positive for Kappa or Lambda or (Tdt negative with CD19 or CD20 or CD22) |
| 8. Mature T-cell | CD3 or cCD3 or (CD2 and (CD2 or CD7 or CD8)) or (CD7 and CD4) or (CD7 and CD8) |
| 9. Plasma cell | Positive for cKappa or cLambda |
| 10. Non-specific | (1) CD14 alone or (2) CD19 positive and Tdt, kappa, lambda ND or (3) CD3 or CD7 or cCD3 positive and Tdt, kappa, lambda ND or (4) Does not meet any definition 1-9. |

Abbreviations:
Tdt = Terminal deoxynucleotidal transferase; cCD3 = cytoplasmic CD3; cCD22 = cytoplasmic CD22; cKappa = cytoplasmic Kappa; cLambda = cytoplasmic Lambda
ND = Not Done For the FCM module 12b, during the data abstraction step, each of the immunophenotype input values are considered "Positive," "Negative" or "Not Done." Similarly, the pattern definitions for the bone marrow module are listed in Table IX and the input values are listed in Table VI above.

TABLE IX
BONE MARROW PATTERN DEFINITIONS

| Pattern | Definition |
| --- | --- |
| 1. Normocellular | Cellularity>30% and<70%, Blasts<5%, Lymphocytes<20%, Plasma cell<10%, Blasts<Promyelocytes+Myelocytes+ Metamyelocytes, Promyelocytes+Myelocytes+ Metamyelocytes<Neutrophils No myeloid or erythroid predominance No qualitative abnormalities |
| 2. Hypocellular | Cellularity<30 % |
| 3. Erythroid predominance hyperplasia | Sum of erythroid precursors>=Sum of myeloid precursors |
| 4. Hypercellular, predominance/ hyperplasia | Cellularity>=70 %, Myeloid>Erythroid, Sum of Myeloid>50 % |
| 5. Megakaryocytic hyperplasia | Megakaryocytes increased |
| 6. Lymphocytosis/ Plasmacytosis | Cellularity>30%, Lymphocytes>20 % or Plasma cells>10% |
| 7. Mononuclear Cell Infiltration | Blasts (non-erythroid)>=30% or Promyelocytes>=30% or Other abnormal mononuclear cells present |
| 8. Foreign Cell Infiltration | Foreign cells present |
| 9. Granulomatous | Granulomas present |
| 10. Bi-hyperplasia | (Patterns 4 and 5 together) or patterns 3 and 5 together) |
| 11. Non-specific | Anything which does not meet any definition 1-10. |

In step 60, the patterns which remain after step 58 are then considered. Considering again the peripheral blood module 12a, if all of the specific patterns have been eliminated in step 58, i.e., in mathematical and computer terms, only the empty set, designated [ ], remains, then the non-specific pattern, i.e. pattern 18, is added to the set. In this case, the non-specific pattern becomes the predominant pattern by default. If there was one specific pattern left in the set after step 58, it becomes the predominant pattern. If there is more than one specific pattern left after step 58, the module 12a branches to the "swallowing mechanism," previously described. As noted, this is one of the most important steps in the process and is based on knowledge obtained from standard textbooks of hematology such as those in the electronic textbook 16 previously discussed. This process is based on the established hierarchy of the patterns. Specifically, the patterns remaining in the set of "patterns matched" which are swallowed by other patterns also remaining in the set are listed in Table X below.

TABLE X
PERIPHERAL BLOOD SWALLOWING

| Pattern | Swallows Pattern Numbers |
| --- | --- |
| 1. Normal | NONE |
| 2. Reactive Neutrophilia | 6 (except Plt>1,000,000), 9, 10, 13, 14, 15, 16 |
| 3. Leukoerythroblastic | 2, 5, 6, 8, 9, 10, 11, 12, 13, 14, 15, 16, 17 |
| 4. Abnormal mononuclear cell | 2, 3, 5, 6, 7, 8, 9, 10, 11, 12, 13, 14, 15, 16, 17 |
| 5. Erythrocytosis | 2, 6, 9, 10, 13, 14 |
| 6. Thrombocytosis | 9, 10 (if Plt>1,000,000) |
| 7. Absolute Lymphocytosis | if (Age>5 or Severe) then 2, 3, 5, 6, 8, 9, 10, 11, 12, 13, 14, 15, 16 else 9, 10 |
| 8. Thrombocytopenia | 2, 5, 9, 10, 13, 14, 15, 16 |
| 9. Eosinophilia | 15, 16 |
| 10. Monocytosis | 6 (if Plt 500,000–999,000), 9, 12, 13, 14, 15, 16 |
| 11. Bi-pancytopenia | 2, 5, 6, 10, 13, 14 |
| 12. Leukopenia | 5, 6 (except Plt>1,000,000), 8, 9, 13, 14, 15, 16, 17 |
| 13. Hypochromic and/or microcytic | 6 (except Plt>1,000,000), 9, 14, 15, 16 |
| 14. Macrocytosis | 6, 9, 13, 15, 16 |
| 15. Normochromic, normocytic anemia | 6 (except Plt>1,000,000) |
| 16. Anemia with anisocytosis | 6 (except Plt>1,000,000), 15 |
| 17. Leukemoid | 2, 5, 6, 8, 9, 10, 11, 13, 14, 15, 16 |

For example, if the remaining set contains patterns 4, 8 and 15, then the swallowing mechanism in step eliminates both patterns 8 and 15 from the set because, as can be seen in Table X, pattern 4 "swallows" all of the other patterns, i.e., it is at the top of the hierarchy. In this example, after going through the swallowing mechanism in step 60, pattern 4 becomes the predominant pattern.

The specific rules for the swallowing mechanism in step 60 for the FCM module 12b and the bone marrow module 12c are given in Tables XI and XII respectively, as set forth below.

TABLE XI

FLOW CYTOMETRY SWALLOWING

| Pattern | Swallows - "Patterns Not Excluded With Numbers" |
|---|---|
| 1. Stem Cell | 7, 8, 9 |
| 2. Myeloid | 1, 7, 8, 9 |
| 3. Erythroid | 1, 5, 6, 7, 8, 9 |
| 4. Megakaryocytic | 1, 7, 8, 9 |
| 5. Immature B-cell | 1, 3, 4, 7, 8, 9 |
| 6. Immature T-cell | 1, 3, 4, 7, 8, 9 |
| 7. Mature B-cell | 1, 2, 3, 4, 5, 6, 8, 9 |
| 8. Mature T-cell | 1, 2, 3, 4, 5, 6*, 7, 9 |
| 9. Plasma cell | 1, 2, 3, 4, 5, 6, 7, 8 |
| 10. Non-specific | NONE |

*if CD4+/CD8- or CD4-/CD8+

TABLE XII

BONE MARROW SWALLOWING

| Pattern | Swallows Pattern Numbers |
|---|---|
| 1. Normocellular | NONE |
| 2. Hypocellular | 1, 3, 5 |
| 3. Erythroid predominance/hyperplasia | 1 |
| 4. Hypercellular, myeloid predominance/hyperplasia | 1 |
| 5. Megakaryocytic hyperplasia | 1 |
| 6. Lymphocytosis/plasmacytosis | 1, 3, 4 |
| 7. Mononuclear cell infiltration | 1, 2, 3, 4, 5, 6, 9, 10 |
| 8. Foreign cell infiltration | 1, 2, 3, 4, 5, 6, 9, 10 |
| 9. Granulomatous | 1, 10 |
| 10. Bi-hyperplasia | 1, 3, 4, 5 |

The flow cytometry module 12b does "swallowing" (in step 68) a little bit differently than the hematology module 12a and bone marrow module 12c. In certain cases, two or more patterns can occur simultaneously, e.g., a biphenotypic leukemia can meet the definition of both the myeloid pattern and the immature B-cell pattern. Instead of swallowing patterns from the set "patterns matched," the flow cytometry module 12b keeps track of which patterns have not been excluded because certain antibodies have not been tested, and compares that list (the set "patterns not excluded") with a list of the patterns that have already been positively matched. The positively matched patterns then "swallow" patterns from the "patterns not excluded" list depending on the hierarchy. In this way, if the test results are not conclusive, and the flow cytometry module 12b requests that additional antibodies be studied, the program only asks the user to test for additional possibilities that are logical, i.e., those that remain in the "not yet excluded" list after swallowing has taken place.

The bone marrow module 12c uses the same swallowing mechanism (i.e., swallowing of patterns from the set "patterns matched") as the peripheral blood module 12a.

In step 62, hematology module 12a compares the specific hemogram findings and the preliminary predominant pattern to a series of "rules" taken from the previously referenced standard textbooks of hematology for electronics textbook 16 which generate recommendations such as "no peripheral blood smear is necessary" or "scan the smear," "look at WBC morphology" and "perform a manual differential." The rules for generating this text are of a similar nature to the examples of programming code in appendices 5, 6 and 7. Programming of this type using "if . . . then" statements is well known to those of ordinary skill in the art.

In step 64 hematology module 12a displays the pattern, the hemogram findings (equivalent to the commercially available Coulter® STKS hematology analyzer definitive flags) and recommendations calculated in steps 56, 58 and 60 in normal text to the user. The program also sets certain check boxes on the display 32 such as "RBC agglutination present" depending on the suspect flags indicated by, e.g., the previously referenced Coulter® Educational Series text (FIGS. 6 and 9).

In step 66, the user enters peripheral blood or blood marrow findings interactively with hematology module 12a or bone marrow module 12c, as respectively shown in FIGS. 7, 10, 11, 17 and 18.

FIG. 7 has been previously described. FIG. 10 shows the RBC morphology screen where the technologist 22 has indicated "1+polychromasia" and "1+macrocytes" by clicking on appropriate radio buttons. FIG. 11 is the WBC screen. The technologist 22 has entered the manual differential into a dialog box (not shown) and the system has displayed that differential which included 86% blasts. The technologist 22 has indicated that "auer rods" are present in the blasts by selecting "present" from the drop-down list box. Auer rods are abnormal granules that are only seen in blasts from patients with acute myeloid leukemia. FIG. 17 is the entry screen for bone marrow aspirate data. The physician 24 has indicated the findings "spicules present" and "megakaryocytes decreased" by clicking on the appropriate radio buttons. The bone marrow differential was entered into a dialog box (not shown) and is displayed by the system. FIG. 18 is the screen for inputting the results of special stains on the bone marrow. The physician 24 has input "peroxidase positive blasts" which indicates an acute myeloid leukemia and NSE (non-specific esterase) positive in 90% of the cells (this finding indicates a monocytic leukemia which is designated type M5a in the FAB, i.e., the French-American-British classification of acute myeloid leukemia). Thus, as shown, the user is free to follow the programs suggestions for additional testing (FIG. 9) or not follow them as they wish (FIG. 7). The module 12a or 12c keeps track of the user input and updates the algorithm "input values" automatically during this process. For example, if the STKS "suspect blast" flag was present, input value #17 is set to "17a." If the WBC manual differential showed no blasts, the human input overrides the hematology analyzer input and parameter #17 is set to "17b."

In step 68 "data abstraction," comparison of the raw data with the established ranges for bone marrow module 12c and flow cytometry module 12b takes place. As mentioned above, in this step all of the modules 12a, 12b and 12c go through the pattern matching program including swallowing, if necessary, exactly as in hematology module 12a at steps 56, 58 and 60, except that all of the data is taken into consideration resulting in a final predominant pattern.

In step 70 all of the modules 12a, 12b and 12c branch to a procedure which is a set of "diagnostic rules" for each given predominant pattern. The rules are used to generate the text of the final report, that is the module's final interpretation/recommendations. Examples of the rules to generate text, as previously noted, are given in Appendices 5, 6, and 7. Also, this type of programming uses the technique of "if . . . then" statements well known to those of ordinary skill in the art, and the rules themselves are taken from standard textbooks of hematology as previously referred to for the electronic textbook 16.

In step 72, in conjunction with step 70, and before assembling the final report, the system checks all of the appropriate databases for additional information. This is a very important step in the process. The databases are indexed on the basis of the patient's identification number. Hematology module 12a checks for certain items of clinical history in the demographics portion of database 14 and also for previous blood specimens on the same patient. The "diagnostic rules" within the final pattern, obtained from the referenced standard textbooks of hematology, govern how to use this information to modify the final report as shown illustratively in Appendices 5, 6 and 7.

Flow cytometry module 12b checks for history, blood and/or bone marrow findings, and previous FCM data. Notice that from FIG. 14, the box labelled "Additional Information" is empty. In this patient, the flow cytometry test was performed on the lymph node biopsy before the peripheral blood test was performed. For this reason, there was no peripheral blood information in the database 14 on this patient. In FIG. 15, the designation "L3" in the box "Additional Information" indicates that the system found peripheral blood data in the database 14 and that the technologist had found blasts with "Burkitt's cell morphology" (designated type L3 by the "French-American-British" [FAB] classification of acute lymphoblastic leukemia) on the manual differential of the peripheral blood. The interpretation includes the pattern matched, the differential diagnosis, a correlation of the findings in the database 14 with flow cytometry data, and a recommendation to confirm these results with a bone marrow/aspirate biopsy. Bone marrow module 12c already knows about the current peripheral blood specimen which was retrieved in step 54. Bone marrow module 12c looks up the history, any FCM data (from flow cytometry module 12b's database) and any previous bone marrow report.

In step 74, before generating the final report, the peripheral blood module 12a goes through another procedure to check if any important information was suppressed by the "swallowing" mechanism. This is necessary because some of the findings may be the result of two pathophysiological processes instead of just one disease. If important information is found, this generates text that is called "drop-in" packages. The rules for the use of drop-in packages are specifically stated in Table XIII below.

TABLE XIII

PERIPHERAL BLOOD DROP-IN PACKAGES

| If this pattern was "swallowed": | Then "drop-in" comments when final predominant pattern is: |
|---|---|
| 2 (reactive Neutrophilia) | 8 (thrombocytopenia) |
| | 11 (Bicytopenia but with increased WBC) |
| | 13 (Hypochromic and/or microcytic) |
| 13 (Hypochromic and/or microcytic) | Any pattern except 3 (Leukoerythroblastic) |
| 14 (Macrocytosis) | 2 (Reactive Neutrophilia) |
| | 8 (Thrombocytopenia) |
| | 12 (Leukopenia) |

TABLE XIII-continued

PERIPHERAL BLOOD DROP-IN PACKAGES

| If this pattern was "swallowed": | Then "drop-in" comments when final predominant pattern is: |
|---|---|
| 15 (Normochromic, normocytic anemia) | 7 (Absolute Lymphocytosis) |
| | 8 (Thrombocytopenia) |

For example, according to Table XIII, a macrocytosis drop-in package (pattern #14) will be added in a patient who has a reactive neutrophilia pattern (predominant pattern #2) because the macrocytosis (i.e., enlargement of the red blood cells) is likely to be due to a separate process (e.g., vitamin deficiency) than the one causing the increased number of white blood cells (e.g., an infection). That is, a patient with both macrocytosis and reactive neutrophilia might have both an infection and a vitamin deficiency. The text for a drop-in package is a shortened version of the text generated when that pattern is the predominant pattern.

In step 76 the final interpretation and recommendations are displayed in a user editable field (a "hard copy" of this report can be generated if the laboratory wishes to do so, for example, at printer 39).

For hematology module 12a and flow cytometry module 12b, this "report" contains the patient identification, final predominant pattern (could be more than one in flow cytometry module 12b), the differential diagnosis, a suggested interpretation if the findings are specific enough, and recommendations for additional history or laboratory tests. This is shown in FIG. 14 for the flow cytometry module where the final interpretation of these data are displayed in the scrollable field. The interpretation includes: 1) the pattern matched, "mature B-cell pattern (monoclonal for lambda)"; 2) the differential diagnosis; 3) the findings which suggest the specific diagnosis of (CLL) or "small lymphocytic lymphoma"; and, 4) a recommendation to correlate these results with other available information. FIG. 15 shows correlation with additional information by the designation "L3" as previously discussed.

For bone marrow module 12c, the final report is a bone marrow report as a pathologist would dictate it, including peripheral blood information, a description of all the pertinent bone marrow findings, the results of the FCM immunophenotyping, and a final interpretation and comments. This is shown in FIG. 19 which illustrates the final interpretation screen for the bone marrow module 12c. The screen consists of a scrollable field in which is displayed the final bone marrow report. The patient identification information has been scrolled off at the top of the screen to show the remainder of the interpretation. The report contains: 1) the peripheral blood findings retrieved from the database 14; 2) the highest bone marrow pattern matched in the hierarchy, "mononuclear cell infiltration"; 3) the bone marrow morphologic findings entered by the physician; 4) a summary of the immunology interpretation (flow cytometry module 12c) retrieved from the database 14; and 5) the final interpretation with the FAB classification.

In step 78 the findings and interpretations are coded and saved to the appropriate portion of database 14. The information entered by the technologist 22 or physician 24 by interaction with the various Windows™ controls such as check boxes, radio buttons and drop-down lists are coded in the bitmap scheme described above. There are alphanumeric fields in the database 14 corresponding to each of the screens which can accept user input in a module (e.g., FIG. 6) from the peripheral blood module 12a corresponds to the field #31 "scan of the peripheral blood smear" in the hemogram database (Appendix 2). These fields contains one character for each of the controls on the corresponding screen. The state of each of the controls when the user clicked on the "proceed" button (i.e., for check boxes and radio buttons whether or not it was checked and for drop-down lists the number of the item that was selected) is coded in the appropriate character for that field. As discussed previously throughout the specification, the following appendixes will aid in understanding the invention when viewed with references.

APPENDIX 1: DEMOGRAPHICS DATABASE STRUCTURE

| Field Name: | Field Type: |
|---|---|
| 1. Patient Identification Number | Alphanumeric |
| 2. Patient Name | Alphanumeric |
| 3. Sex | Alphanumeric |
| 4. Date of Birth | Paradox Date (long integer) |
| 5. Race | Alphanumeric |
| 6. Inherited Diseases | Alphanumeric (coded bitmap) |
| 7. Social History | Alphanumeric (coded bitmap) |
| 8. Previous Surgery | Alphanumeric (coded bitmap) |
| 9. Drug History | Alphanumeric (coded bitmap) |
| 10. Date of Drug History | Paradox Date (long integer) |
| 11. Cancer History | Alphanumeric (coded bitmap) |
| 12. Autoimmune History | Alphanumeric (coded bitmap) |
| 13. Endocrine History | Alphanumeric (coded bitmap) |
| 14. Impaired Immunity | Alphanumeric (coded bitmap) |
| 15. Lab Tests | Alphanumeric (coded bitmap) |

APPENDIX 2: HEMOGRAM DATABASE STRUCTURE

| Field Name: | Field Type: |
|---|---|
| 1. Date of Specimen | Paradox Date (long integer) |
| 2. Time of Specimen | Alphanumeric |
| 3. Patient Identification Number | Alphanumeric |
| 4. Sequence Number | Alphanumeric |
| 5. Cassette/Position | Alphanumeric |
| 6. Patient Location | Alphanumeric |
| 7. Physician | Alphanumeric |
| 8. User Field #1 | Alphanumeric |
| 9. User Field #2 | Alphanumeric |
| 10. User Field #3 | Alphanumeric |
| 11. Comments | Alphanumeric |
| 12. RBC Count | Numeric |
| 13. Hemoglobin | Numeric |
| 14. Hematocrit | Numeric |
| 15. MCV | Numeric |
| 16. MCH | Numeric |
| 17. MCHC | Numeric |
| 18. RDW | Numeric |
| 19. Platelet Count | Numeric |
| 20. WBC Count | Numeric |
| 21. Neutrophils [%] | Numeric |
| 22. Lymphocytes [%] | Numeric |
| 23. Monocytes [%] | Numeric |
| 24. Eosinophils [%] | Numeric |
| 25. Basophils [%] | Numeric |
| 26. WBC Population Flag | Alphanumeric |
| 27. RBC Population Flag | Alphanumeric |
| 28. Platelet Population Flag | Alphanumeric |
| 29. Suspect Flags | Alphanumeric (coded bitmap) |
| 30. Preliminary Pattern | Numeric |
| 31. Scan of Peripheral Blood Smear | Alphanumeric (coded bitmap) |
| 32. RBC Morphology | Alphanumeric (coded bitmap) |
| 33. Organisms | Alphanumeric |
| 34. Manual Differential -- Neutrophils | Numeric |
| 35. Manual Differential -- Bands | Numeric |
| 36. Manual Differential -- Lymphocytes | Numeric |

APPENDIX 2: HEMOGRAM DATABASE STRUCTURE

| Field Name: | Field Type: |
|---|---|
| 37. Manual Differential -- Monocytes | Numeric |
| 38. Manual Differential -- Eosinophils | Numeric |
| 39. Manual Differential -- Basophils | Numeric |
| 40. Manual Differential -- NRBCs | Numeric |
| 41. Manual Differential -- Blasts | Numeric |
| 42. Manual Differential -- Promyelocytes | Numeric |
| 43. Manual Differential -- Myelocytes | Numeric |
| 44. Manual Differential -- Metamyelocytes | Numeric |
| 45. Other Mononuclear Cells (OMNC) | Numeric |
| 46. Type of OMNC | Alphanumeric |
| 47. Manual Platelet Count | Numeric |
| 48. WBC Morphology | Alphanumeric (coded bitmap) |
| 49. WBC Inclusions | Alphanumeric |
| 50. Final Pattern | Numeric |
| 51. Reticulocyte Count | Numeric |

APPENDIX 3: FLOW CYTOMETRY DATABASE STRUCTURE

| Field Name: | Field Type: |
|---|---|
| 1. Specimen Identification Number | Alphanumeric |
| 2. Patient Identification Number | Alphanumeric |
| 3. Clinical Information | Alphanumeric |
| 4. Specimen Type | Alphanumeric |
| 5. Specimen Date | Paradox Date (long integer) |
| 6. CD1a | Alphanumeric |
| 7. CD2 | Alphanumeric |
| 8. CD3 | Alphanumeric |
| 9. CD4 | Alphanumeric |
| 10. CD5 | Alphanumeric |
| 11. CD7 | Alphanumeric |
| 12. CD8 | Alphanumeric |
| 13. CD10 | Alphanumeric |
| 14. CD11c | Alphanumeric |
| 15. CD13 | Alphanumeric |
| 16. MY4 | Alphanumeric |
| 17. Mo2 | Alphanumeric |
| 18. CD16 | Alphanumeric |
| 19. CD19 | Alphanumeric |
| 20. CD20 | Alphanumeric |
| 21. CD22 | Alphanumeric |
| 22. CD25 | Alphanumeric |
| 23. CD33 | Alphanumeric |
| 24. CD34 | Alphanumeric |
| 25. CD41 | Alphanumeric |
| 26. CD56 | Alphanumeric |
| 27. CD57 | Alphanumeric |
| 28. CD61 | Alphanumeric |
| 29. Kappa | Alphanumeric |
| 30. Lambda | Alphanumeric |
| 31. Ia (HLA-DR) | Alphanumeric |
| 32. Glycophorin A | Alphanumeric |
| 33. Cytoplasmic Kappa | Alphanumeric |
| 34. Cytoplasmic Lambda | Alphanumeric |
| 35. Tdt | Alphanumeric |
| 36. Myeloperoxidase Antibody | Alphanumeric |
| 37. Cytoplasmic CD3 | Alphanumeric |
| 38. Cytoplasmic CD22 | Alphanumeric |
| 39. Cytoplasmic mu | Alphanumeric |
| 40. Myeloperoxidase Cytochemistry | Alphanumeric |
| 41. CD45 | Alphanumeric |
| 42. CD71 | Alphanumeric |
| 43. Pattern | Numeric |
| 44. Absolute CD4 Count | Numeric |
| 45. Size of Abnormal Cells | Alphanumeric |
| 46. Percent Abnormal Cells | Numeric |
| 47. DNA Index | Numeric |
| 48. Total S-phase | Numeric |
| 49. Tumor S-phase | Numeric |
| 50. Name of Immunophenotyping Panel | Alphanumeric |

APPENDIX 4: BONE MARROW DATABASE STRUCTURE

| Field Name: | Field Type: |
| --- | --- |
| 1. Specimen Identification Number | Alphanumeric |
| 2. Specimen Date | Paradox Date (long integer) |
| 3. Patient Identification Number | Alphanumeric |
| 4. Specimen Type (aspirate/biopsy/touch prep) | Alphanumeric |
| 5. Aspirate Cellularity [%] | Numeric |
| 6. Differential -- Blasts | Numeric |
| 7. Differential -- Promyelocytes | Numeric |
| 8. Differential -- Myelocytes | Numeric |
| 9. Differential -- Metamyelocytes | Numeric |
| 10. Differential -- Neutrophils/Bands | Numeric |
| 11. Differential -- Monocytes | Numeric |
| 12. Differential -- Eosinophils | Numeric |
| 13. Differential -- Basophils | Numeric |
| 14. Differential -- Lymphocytes | Numeric |
| 15. Differential -- Plasma Cells | Numeric |
| 16. Differential -- Early Erythrocyte Precursors | Numeric |
| 17. Differential -- Late Erythrocytes Precursors | Numeric |
| 18. Other Mononuclear Cells (OMNC) | Numeric |
| 19. Type of OMNC | Alphanumeric |
| 20. Type of Blast Morphology | Alphanumeric |
| 21. Aspirate Features | Alphanumeric (coded bitmap) |
| 22. Biopsy Cellularity [%] | Numeric |
| 23. Biopsy Findings | Alphanumeric (coded bitmap) |
| 24. Ring Sideroblasts [%] | Numeric |
| 25. Non-Specific Esterase Stain [% Positive] | Numeric |
| 26. Special Stains | Alphanumeric (coded bitmap) |
| 27. Pattern | Numeric |

APPENDIX 5: EXAMPLE CODE FROM PERIPHERAL BLOOD MODULE - PATTERN 7

```
procedure Pattern7(HWindow:HWnd);
begin
With ACase^ do
begin
StrCat(S,#13#10);
if (Age<40) or (AbsLymph<15.0) then
StrCat(S,'The differential diagnosis is a REACTIVE LYMPHOCYTOSIS
versus a LYMPHOPROLIFERATIVE DISORDER.'#13#10#13#10);
if (Age>= 40) and (AbsLymph>= 15.0) then
StrCat(S,'The findings suggest a chronic LYMPHOPROLIFERATIVE
DISORDER in this age group. '#13#10#13#10);
if (Age<35) and (Ninput[19] = '19a') then
StrCat(S,'Serologic studies may be helpful to rule-out INFECTIOUS
MONONUCLEOSIS.'#13#10#13#10);
if (Age>=40) and (AbsLymph>=15.0) and (CLFLag=FALSE) and
(SezFlag=FALSE) and (ATLLFLag=FALSE) then
begin
StrCat(S,'The marked absolute lymphocytosis composed of small,
"mature-appearing" lymphocytes');
StrCat(S,'is suggestive of CLL.'#13#10#13#10);
if SmudgeFlag then StrCat(S,'Smudge cells are commonly seen in CLL.'
#13#10#13#10);
```

APPENDIX 5: EXAMPLE CODE FROM PERIPHERAL BLOOD MODULE - PATTERN 7

```
end;
StrCat(S,'Physical examination for lymphadenopathy and
hepatosplenomegaly may be helpful.'#13#10#13#10);
if Ninput[3]<"3d' then
begin
if (SpherocyteFlag) and (PolychromFlag) and (SchistoFlag=FALSE) then
begin
StrCat(S,'The presence of spherocytes and polychromasia suggests an
immune hemolytic ');
StrCat(S,'anemia. A COOMB"S test may be helpful.'#13#10#13#10);
end;
if (SchistoFlag) and (PolychromFlag) then
begin
StrCat(S,'The presence of schistocytes and polychromasia suggests a
microangiopathic ');
StrCat(S,'hemolytic anemia vs valvular heart disorder. ');
StrCat(S,'The exact etiology must be determined clinically.'
#13#10#13#10);
end
end;
if (LGLFlag) and (AbsLymph<15.0) then
begin
StrCat(S,'The findings suggest a LARGE GRANULAR
LYMPHOCYTOSIS.'#13#10#13#10);
StrCat(S,'Clinical history and serologic studies to rule-out rheumatoid
arthritis may be helpful.'#13#10#13#10);
end;
if (Age<40) or (AbsLymph<15.0) then
begin
StrCat(S,'If a LYMPHOPROLIFERATIVE DISORDER is suspected,
IMMUNOPHENOTYPING by
FLOW CYTOMETRY and/or ');
StrCat(S,'a BONE MARROW ASPIRATE/BIOPSY may be helpful.'
#13#10#13#10);
end;
if (Age>=40) and (AbsLymph>=15.0) then
begin
StrCat(S,'The following test may be helpful'#13#10);
StrCat(S,'IMMUNOPHENOTYPING by FLOW CYTOMETRY, BONE
MARROW ASPIRATE/BIOPSY.'#13#10#13#10);
end;
end
end;
```

APPENDIX 6: EXAMPLE CODE FROM FLOW CYTOMETRY MODULE FROM PATTERN 8

```
if (8 in PatternMatch) then
begin
if (Markers[CD2].Status<>'Not Done') and (Markers[CD3].Status<>'Not Done') and
(Markers[CD5].Status<>'Not Done') and (Markers[CD7].Status<>'Not Done') then
begin
if (Markers[CD2].Status='NEG') or (Markers[CD3].Status='NEG') or
(Markers[CD5].Status ='NEG')
or (Markers[CD7].Status='NEG') then AberrantTFlag:=TRUE;
```

-continued

APPENDIX 6: EXAMPLE CODE FROM FLOW CYTOMETRY MODULE FROM PATTERN 8

```
end;
if FewMalignant=FALSE then StrCat(IS,'The differential diagnosis includes: '#13#10)
else StrCat(IS,'The differential diagnosis is suggestive of: '#13#10);
if Markers[CD8].Status='POS') and (Markers[CD4].Status='NEG') then
StrCat(IS,'T-Cell lymphoproliferative disorders (LGL, T-PLL, ATLL, CTCL), ')
else
StrCat(IS,'T-Cell lymphoproliferative disorders (T-PLL, CTCL, ATLL, LGL), ');
if ((DNAIndex=0.0) or (DNAIndex=1.0)) and (AberrantTFlag=FALSE) then
StrCat(IS, 'Non-Hodgkin''s Lymphomas, and Reactive Conditions.');
if ((DNAIndex<>0.0) and (DNAIndex<>1.0)) or (AberrantTFlag) then StrCat(IS,'and Non-
Hodgkin''s
Lymphomas.');
StrCat(IS,#13#10#13#10);
if (8 in PatternMatch) and (Markers[CD4].Status='POS') and (Markers[CD8].Status='NEG')
and (StrPos(TempString,'Sezary') <> nil) then
begin
StrCat(IS,'The helper T-cell phenotype is consistent with the Sezary cells ');
StrCat(IS,'identified on the peripheral blood smear.'#13#10#13#10);
end;
if AberrantTFlag then
StrCat(IS,'The findings suggest an aberrant T-phenotype with loss of a pan-T
marker.'#13#10#13#10);
if Markers[CD25].Status='POS') and (Markers[CD4].Status='POS') and
(StrPos(TempString,'ATLL') = nil)
then
begin
StrCat(IS,'CD25 positivity is suggestive of ATLL. The HTLV-I status should ');
StrCat(IS,'be determined to confirm the diagnosis.'#13#10#13#10);
end;
if Markers[CD25].Status='POS') and (StrPos(TempString,'ATLL') <> nil) then
begin
StrCat(IS,'The CD25 positivity is consistent with the presence of circulating "flower" cells. ');
StrCat(IS,'The HTLV-I status should be determined to confirm the diagnosis.'#13#10#13#10);
end;
if (Markers[CD16].Status ='POS') or #Markers[CD56].Status ='POS')
or (Markers[CD57].Status='POS') then
begin
StrCat(IS,'The positive marker(s) from the group CD16/CD56/CD57 are suggestive of LGL.');
StrCat(IS,#13#10#13#10);
end
end;
```

APPENDIX 7: EXAMPLE CODE FROM BONE MARROW MODULE
(Myelodysplastic Syndromes)

```
procedure MDS;
begin
With ACase^ do
begin
MDSFlag:=FALSE;
if (BMBlasts<5) and (RS<=15) and (PBBlasts<=1) and ((PBMono*WBC/100)<=1.0)
and (Hgb<12) and (AuerFlag=FALSE) and (BMAuerFlag=FALSE) and (FagotFlag=FALSE)
and
BMFagotFlag=FALSE) then
begin
StrCat(S,'Refractory Anemia.');
MDSFlag:=TRUE;
end;
if (BMBlasts<5) and (RS<=15) and (PBBlasts<=1) and ((PBMono*WBC/100)<=1.0)
and (Hgb>=12) and ((WBC<4.0) or (PLT<150)) and (AuerFlag=FALSE) and
(BMAuerFlag=FALSE)
and (FagotFlag=FALSE) and (BMFagotFlag=FALSE) then
begin
StrCat(S, 'Refractory Cytopenia.');
MDSFlag:=TRUE;
end;
if (BMBlasts<5) and (RS>15) and (PBBlasts<=1) and ((PBMono*WBC/100)<=1.0)
and (Hgb<12) and (AuerFlag=FALSE) and (BMAuerFlag=FALSE) and (FagotFlag=FALSE)
and (BMFagotFlag=FALSE) then
begin
StrCat(S,'Refractory Anemia with Ring Sideroblasts.');
MDSFlag:=TRUE;
end;
if (BMBlasts>=5) and (BMBlasts<=20) and (PBBlasts<5) and ((PBMono*WBC/100)<=1.0)
```

-continued

APPENDIX 7: EXAMPLE CODE FROM BONE MARROW MODULE
(Myelodysplastic Syndromes)

```
and (Hgb<12) then
begin
StrCat(S,'Refractory Anemia with Excess of Blasts.');
MDSFlag:=TRUE;
end;
if (CancerHx[0]<='0') and (BMBlasts<=20) and (PBBlasts<5) and
(PBMono*WBC/100)>1.0) and (PBBaso*WBC<0.2 and ((PBPro+PBMyel+PBMeta)<=15)
and (AuerFlag=FALSE)
and (BMAuerFlag=FALSE) and (FagotFlag=FALSE) and (BMFagotFlag=FALSE) then
begin
if NSE>=20 then StrCat(S,'Chronic myelomonocytic leukemia.');
if (NSE<20) and (BMBlasts>=5) and (Hgb<12) then StrCat(S,'RAEB with peripheral
monocytosis.');
if (NSE<20) and (BMBlasts<5) and (Hgb<12) then StrCat(S,'"Refractory"anemia with
peripheral
monocytosis.');
if NSE=-1 then
begin
StrCat(S,#13#10#13#10);
StrCat(S,'NOTE: ');
StrCat(S,'A nonspecific esterase stain is needed to rule-out CMMoL.');
end;
MDSFlag:=TRUE;
end;
if ((BMBlasts>20) and (BMBlasts<30)) or (PBBlasts>=5) or (AuerFlag) or (BMAuerFlag)
and (Hgb<12) then
begin
StrCat(S,'Refractory Anemia with Excess Blasts in Transformation.');
MDSFlag:=TRUE;
end
end
end;
```

Having thus described the invention, the same will become better understood from the appended claims wherein it is described in a non-limiting manner.

What is claimed is:

1. A method of interpreting hematopathology test results to arrive at a diagnosis of a patient comprising the steps of:
    conducting at least one hematopathology test on at least one sample from a patient;
    retrieving data from said at least one hematopathology test for the patient and storing said hematopathology test data in a database;
    comparing said hematopathology test data with at least one set of a predetermined number of hematopathology patterns, each of said hematopathology patterns corresponding to different patient conditions and said patterns arranged in a predetermined hierarchy, to determine which patterns match said hematopathology test data in said database;
    displaying the patterns matched, with recommendations corresponding to the matched patterns for one of no additional testing and one of a plurality of identified additional testing, the results of which are likely to lead to a diagnosis of the patient's condition;
    conducting any additional testing recommended, retrieving the data therefrom and storing it in said database with said hematopathology test data;
    comparing said additional test data and hematopathology test data with said predetermined number of patterns, to determine which patterns match said hematopathology test data in said database; and
    identifying and displaying the highest ranked pattern in said hierarchy to arrive at a differential diagnosis of the patient's condition.

2. A method as in claim 1 wherein said hematopathology test is a hematology test in which peripheral blood analysis is conducted.

3. A method as in claim 1 wherein said hematopathology test is a hematology test in which peripheral blood analysis is conducted.

4. A method as in claim 3 wherein said additional test is a review of a blood smear from the patient, and further comprising one of inputting additional data from the blood smear review and correcting for any erroneous data input into said database from said hematology test.

5. A method as in claim 4 wherein said differential diagnosis includes recommendations for additional testing comprised of flow cytometry testing of a sample from the patient, and further comprising:
    conducting said flow cytometry testing;
    inputting the flow cytometry test data from said testing into said database with said hematology test data;
    comparing said flow cytometry test data and hematology test data with said at least one set of a predetermined number of patterns, to determine which patterns match said hematology test data and flow cytometry test data in said database; and
    identifying and displaying at least one highest ranked pattern in said hierarchy to arrive at a differential diagnosis of the patient's condition.

6. A method as in claim 4 wherein said differential diagnosis includes recommendations for additional testing comprised of bone marrow testing of a sample from the patient, and further comprising:
    conducting said bone marrow testing;
    inputting the bone marrow test data from said testing into said database with said hematology test data;
    comparing said bone marrow test data and hematology test data with said at least one set of a predetermined number of patterns, to determine which patterns match said hematology test data and bone marrow test data in said database; and identifying and displaying the highest ranked pattern in said hierarchy to arrive at a differential diagnosis of the patient's condition.

7. A method of interpreting hematopathology test results to arrive at a diagnosis of a patient; comprising the steps of:

conducting at least one hematopathology test on at least one sample from a patient, said hematopathology test being a flow cytometry test;

retrieving data from said flow cytometry test for the patient and storing said flow cytometry test data in a database;

comparing said flow cytometry test data with at least one set of a predetermined number of hematopathology patterns previously stored in said database, each of said hematopathology patterns corresponding to different patient conditions and said patterns arranged in a predetermined hierarchy to determine which patterns match said flow cytometry test data in said database; and identifying and displaying at least one highest ranked pattern in said hierarchy to arrive at a differential diagnosis of the patient's condition.

8. A method as in claim 7 wherein said hematopathology test is a bone marrow test, and wherein said comparing step is conducted by comparing said test data from said bone marrow test and data from a hematology test previously entered into said database with said at least one set of patterns.

9. A method as in claim 7 wherein said hematopathology test is a flow cytometry test, and wherein said comparing step is conducted by comparing said test data from said flow cytometry test and data from a bone marrow test previously entered into said database with said at least one set of patterns.

10. A method as in claim 7 wherein said hematopathology test is a hematology test, and wherein said comparing step is conducted by comparing said test data from said hematology test and data from a flow cytometry test previously entered into said database with said at least one set of patterns.

11. A method as in claim 7 wherein said hematopathology test is a hematology test, and wherein said comparing step is conducted by comparing said test data from said hematology test and data from a bone marrow test previously input into said database with said patterns.

12. A method as in claim 7 wherein said hematopathology test is a bone marrow test, and wherein said comparing step is conducted by comparing said test data from said bone marrow test and data from a flow cytometry test previously input into said database with said patterns.

13. A system for interpreting hematopathology test results to arrive at a diagnosis of a patient, comprising:

database storage means for storing a database of test results from hematopathology tests for specific patients;

knowledge base/inference engine means for storing at least one set of a predetermined number of patterns corresponding to specific patient conditions, including a normal condition, with said patterns arranged in a predetermined hierarchy, and for storing instructions for comparing said patterns to said database of test results for determining which patterns are matched;

comparing means for comparing data from said tests for a specific patient with said patterns to determine which patterns are matched and which pattern is highest in the hierarchy;

input means for inputting said data from test results into said database; and output means for outputting the results of said comparison by said comparing means, said results being comprised of at least one of the highest ranked pattern, a differential diagnosis and recommendations for additional testing.

14. A system as in claim 13 wherein said input means comprises a keyboard, said output means comprises a display, said database storage means and knowledge base storage means comprise a "direct access storage device" (DASD), and said comparing means comprises a central processing unit.

15. A system as in claim 14 wherein said input means further comprises interface means connected to said comparing means and configured for being connected to a hematology analyzer for having test results therefrom directly input into said database storage means.

16. A system as in claim 14 wherein said input means further comprises interface means connected to said comparing means and configured for being connected to a flow cytometry analyzer for having test results therefrom directly input into said database storage means.

17. A system as in claim 13 further comprising textbook storage means for storing textbook reference data about hematopathology and connected for allowing a user to make reference to hematopathology reference data when reviewing the results of any comparison conducted with said system.

18. A system as in claim 14 further comprising textbook storage means for storing textbook reference data about hematopathology and connected for allowing a user to make reference to hematopathology reference data when reviewing the results of any comparison conducted with said system and wherein said textbook storage means comprises a "direct access storage device" (DASD).

* * * * *